United States Patent
Anderson et al.

(10) Patent No.: US 6,794,173 B2
(45) Date of Patent: Sep. 21, 2004

(54) DENDRITIC CELL TRANSMEMBRANE SERINE PROTEASE

(75) Inventors: Dirk M. Anderson, Seattle, WA (US); G. Duke Virca, Seattle, WA (US)

(73) Assignee: Immunex Corporation, Seattle, WA (US)

(*) Notice: Subject to any disclaimer, the term of this patent is extended or adjusted under 35 U.S.C. 154(b) by 0 days.

(21) Appl. No.: 10/177,661

(22) Filed: Jun. 20, 2002

(65) Prior Publication Data

US 2003/0082783 A1 May 1, 2003

Related U.S. Application Data

(60) Provisional application No. 60/299,606, filed on Jun. 20, 2001.

(51) Int. Cl.[7] .................................................. C12N 9/64
(52) U.S. Cl. ...................................... 435/226; 530/324
(58) Field of Search ................................ 435/226, 212; 530/324

(56) References Cited

FOREIGN PATENT DOCUMENTS

WO      WO 00/68247      11/2000

OTHER PUBLICATIONS

Afar et al, Catalytic cleavage of the androgen–regulated TMPRSS2 protease results in its secretion by prostate and prostate cancer epithelia. Cancer Res. Feb. 15, 2001; 61(4):1686–92.*
Xiao et al, U.S. application 09/879,792 PGPub US20020061850 SEQ ID No.: 12 May 23, 2002 Priority Date Apr. 13, 2001.*
Ausubel, et al, Introduction to expression by fusion prtein vectors In: Current Protocols in Molecular Biology 1994 Unit 16.4.*
Tsuruta et al, Soluble vascular cell adhesion molecule (VCAM)–Fc fusion protein induces leukotriene C4 secretion in platelet–activating factor–stimulated eosinophils. J Leukoc Biol. Jan. 1999;65(1):71–9.*
Weill et al, Functional characterization and potential applications for enhanced green fluorescent protein– and epitope–fused J Neurochem. Aug. 1999;73(2):791–801.*
Lau et al Interaction of the N–methyl–D–aspartate receptor complex with a novel synapse–associated protein, SAP102. J Biol Chem. Aug. 30, 1996;271(35):21622–8.*
Shugars et al, Biophysical characterization of recombinant proteins expressing the leucine zipper–like domain of the human immunodeficiency virus type 1 transmembrane protein gp41. J Virol. May 1996;70(5):2982–91.*
Sorensen et al, Polymerization of IgA and IgM: roles of Cys309/Cys414 and the secretory tailpiece. J Immunol. Mar. 15, 1999;162(6):3448–55.*
Accession No. AAD02322, Human serine protease #3, encoding HATEE38 cDNA clone. Ruben et al Mar. 28, 2001.
Accession No. AP000757, Homo sapiens genomic DNA, chromosome 11q clone: RP11–728F11, complete sequences. Hattori et al Feb. 22, 2001.
Kim, D.R. et al., "Cloning and expression of novel mosaic serine proteases with and without a transmembrane domain from human lung," *Biochemica et Biophysica Acta.* 1518: 204–209, 2001.

* cited by examiner

Primary Examiner—Rebecca E. Prouty
Assistant Examiner—Sheridan L. Swope
(74) Attorney, Agent, or Firm—Patricia Anne Perkins

(57) ABSTRACT

Isolated Dendritic Cell Transmembrane Serine Proteases (DCTSPs), DNAs encoding such DCTSPs, and pharmaceutical and/or diagnostic compositions made therefrom, are disclosed. The isolated DCTSPs can be used to hydrolyze peptide bonds. The DCTSPs are also useful in screening for inhibitors or agonists thereof.

4 Claims, 1 Drawing Sheet

```
hu_chymo     1                                                         42
             CGVPAIHPVL SGLSRIVNGE DAVPGSWPWQ VSLQDKTGFH FCGGSLISED
             **         *  ****             *         *   *  ** **
DCTSP        LR ...M  T           G A  L SDSK         HFG .T    I  T DAQ
             227                                                       261 hu_chymo                                                               136
             WVVTAAHCGV RTSDVVVAG. EFDQGSD..E ENIQVLKIAK VFKNPKFSIL
             *  ******  *   *      *         *  *    *  *  *
DCTSP  5758  L   FF V REK LE W KVYA TSNLH QLPEAAS  E III SNYTDE
       276277 hu_chymo     102                             122                       136
             TVNNDITLLK LATPARFSQT VSAVCLPSAD DDFPAGTLCA TTGWGKTKYN
                **   *  *   *      *   *     *         *      *
DCTSP        EDDY A MR   SK LTL AH IHPA   MHG QT SLNET W  I  F    RET
             324                                                       358 hu_chymo                              168                  182         191
             ANKTPDKLQQ AALPLLSNAE CKK..SWGRR ITDVMICAG. .ASGVSSCMG
               **       **           *        *    ***  *   **  **
DCTSP        DD SPF  RE VQVN IDFKK NDYLVYDSY L PR M   D LRG  RD  Q
             390                              406                      417 hu_chymo     195  201                220
             DSGGPLVCQK DGAWTLVGIV SWGSDTCS TS SPGVYARVTK LIPWVQKILA
             *********  *   *     *  *     *  *     *    *   *   *
DCTSP        EQ NNR  Y A VT      .TG GQRN  K  TK  E VL  IYSKME
             421      427                  445 hu_chymo     AN------
             SEVRFRKS
DCTSP
```

Figure 1

SEQUENCE LISTING

```
<160> NUMBER OF SEQ ID NOS: 6

<210> SEQ ID NO 1
<211> LENGTH: 1434
<212> TYPE: DNA
<213> ORGANISM: Homo sapiens
<220> FEATURE:
<221> NAME/KEY: CDS
<222> LOCATION: (1)..(1434)
<223> OTHER INFORMATION:

<400> SEQUENCE: 1 atg gga caa aat tca ttc att cat tca att gac ttt gag ccc cat aaa        48
Met Gly Gln Asn Ser Phe Ile His Ser Ile Asp Phe Glu Pro His Lys
1               5                   10                  15 atc tca ttc caa ctt ctg ggg tgg agt ggt cct cac ggg gcc ctc ctg        96
Ile Ser Phe Gln Leu Leu Gly Trp Ser Gly Pro His Gly Ala Leu Leu
            20                  25                  30 ggc cac agt ctt gtt tcc ccc acc ctc tcc atc tcg tcg gac tcc tct       144
Gly His Ser Leu Val Ser Pro Thr Leu Ser Ile Ser Ser Asp Ser Ser
        35                  40                  45 cca gcc tca tat tcc cct gct gcc gcc ctg cta cta ggt acg agc ctg       192
Pro Ala Ser Tyr Ser Pro Ala Ala Ala Leu Leu Leu Gly Thr Ser Leu
    50                  55                  60 ccc aag ttc acc tgg cgg gag ggc cag aag cag cta ccg ctc atc ggg       240
Pro Lys Phe Thr Trp Arg Glu Gly Gln Lys Gln Leu Pro Leu Ile Gly
65                  70                  75                  80 tgc gtg ctc ctc ctc att gcc ctg gtg gtt tcg ctc atc atc ctc ttc       288
Cys Val Leu Leu Leu Ile Ala Leu Val Val Ser Leu Ile Ile Leu Phe
                85                  90                  95
```

```
                                                                -continued cag ttc tgg cag ggc cac aca ggg atc agg tac aag gag cag agg gag        336
Gln Phe Trp Gln Gly His Thr Gly Ile Arg Tyr Lys Glu Gln Arg Glu
            100                 105                 110 agc tgt ccc aag cac gct gtt cgc tgt gac ggg gtg gtg gac tgc aag        384
Ser Cys Pro Lys His Ala Val Arg Cys Asp Gly Val Val Asp Cys Lys
        115                 120                 125 ctg aag agt gac gag ctg ggc tgc gtg agg ttt gac tgg gac aag tct        432
Leu Lys Ser Asp Glu Leu Gly Cys Val Arg Phe Asp Trp Asp Lys Ser
    130                 135                 140 ctg ctt aaa atc tac tct ggg tcc tcc cat cag tgg ctt ccc atc tgt        480
Leu Leu Lys Ile Tyr Ser Gly Ser Ser His Gln Trp Leu Pro Ile Cys
145                 150                 155                 160 agc agc aac tgg aat gac tcc tac tca gag aag acc tgc cag cag ctg        528
Ser Ser Asn Trp Asn Asp Ser Tyr Ser Glu Lys Thr Cys Gln Gln Leu
                165                 170                 175 ggt ttc gag agt gct cac cgg aca acc gag gtt gcc cac agg gat ttt        576
Gly Phe Glu Ser Ala His Arg Thr Thr Glu Val Ala His Arg Asp Phe
            180                 185                 190 gcc aac agc ttc tca atc ttg aga tac aac tcc acc atc cag gaa agc        624
Ala Asn Ser Phe Ser Ile Leu Arg Tyr Asn Ser Thr Ile Gln Glu Ser
        195                 200                 205 ctc cac agg tct gaa tgc cct tcc cag cgg tat atc tcc ctc cag tgt        672
Leu His Arg Ser Glu Cys Pro Ser Gln Arg Tyr Ile Ser Leu Gln Cys
    210                 215                 220 tcc cac tgc gga ctg agg gcc atg acc ggg cgg atc gtg gga ggg gcg        720
Ser His Cys Gly Leu Arg Ala Met Thr Gly Arg Ile Val Gly Gly Ala
225                 230                 235                 240 ctg gcc tcg gat agc aag tgg cct tgg caa gtg agt ctg cac ttc ggc        768
Leu Ala Ser Asp Ser Lys Trp Pro Trp Gln Val Ser Leu His Phe Gly
                245                 250                 255 acc acc cac atc tgt gga ggc acg ctc att gac gcc cag tgg gtg ctc        816
Thr Thr His Ile Cys Gly Gly Thr Leu Ile Asp Ala Gln Trp Val Leu
            260                 265                 270 act gcc gcc cac tgc ttc ttc gtg acc cgg gag aag gtc ctg gag ggc        864
Thr Ala Ala His Cys Phe Phe Val Thr Arg Glu Lys Val Leu Glu Gly
        275                 280                 285 tgg aag gtg tac gcg ggc acc agc aac ctg cac cag ttg cct gag gca        912
Trp Lys Val Tyr Ala Gly Thr Ser Asn Leu His Gln Leu Pro Glu Ala
    290                 295                 300 gcc tcc att gcc gag atc atc atc aac agc aat tac acc gat gag gag        960
Ala Ser Ile Ala Glu Ile Ile Ile Asn Ser Asn Tyr Thr Asp Glu Glu
305                 310                 315                 320 gac gac tat gac atc gcc ctc atg cgg ctg tcc aag ccc ctg acc ctg       1008
Asp Asp Tyr Asp Ile Ala Leu Met Arg Leu Ser Lys Pro Leu Thr Leu
                325                 330                 335 tcc gct cac atc cac cct gct tgc ctc ccc atg cat gga cag acc ttt       1056
Ser Ala His Ile His Pro Ala Cys Leu Pro Met His Gly Gln Thr Phe
            340                 345                 350 agc ctc aat gag acc tgc tgg atc aca ggc ttt ggc aag acc agg gag       1104
Ser Leu Asn Glu Thr Cys Trp Ile Thr Gly Phe Gly Lys Thr Arg Glu
        355                 360                 365 aca gat gac aag aca tcc ccc ttc ctc cgg gag gtg cag gtc aat ctc       1152
Thr Asp Asp Lys Thr Ser Pro Phe Leu Arg Glu Val Gln Val Asn Leu
    370                 375                 380 atc gac ttc aag aaa tgc aat gac tac ttg gtc tat gac agt tac ctt       1200
Ile Asp Phe Lys Lys Cys Asn Asp Tyr Leu Val Tyr Asp Ser Tyr Leu
385                 390                 395                 400 acc cca agg atg atg tgt gct ggg gac ctt cgt ggg ggc aga gac tcc       1248
Thr Pro Arg Met Met Cys Ala Gly Asp Leu Arg Gly Gly Arg Asp Ser
                405                 410                 415
```

-continued

```
tgc cag gga gac agc ggg ggg cct ctt gtc tgt gag cag aac aac cgc    1296
Cys Gln Gly Asp Ser Gly Gly Pro Leu Val Cys Glu Gln Asn Asn Arg
        420                 425                 430 tgg tac ctg gca ggt gtc acc agc tgg ggc aca ggc tgt ggc cag aga    1344
Trp Tyr Leu Ala Gly Val Thr Ser Trp Gly Thr Gly Cys Gly Gln Arg
    435                 440                 445 aac aaa cct ggt gtg tac acc aaa gtg aca gaa gtt ctt ccc tgg att    1392
Asn Lys Pro Gly Val Tyr Thr Lys Val Thr Glu Val Leu Pro Trp Ile
450                 455                 460 tac agc aag atg gag agc gag gtg cga ttc aga aaa tcc taa            1434
Tyr Ser Lys Met Glu Ser Glu Val Arg Phe Arg Lys Ser
465                 470                 475

<210> SEQ ID NO 2
<211> LENGTH: 477
<212> TYPE: PRT
<213> ORGANISM: Homo sapiens

<400> SEQUENCE: 2

Met Gly Gln Asn Ser Phe Ile His Ser Ile Asp Phe Glu Pro His Lys
1               5                   10                  15

Ile Ser Phe Gln Leu Leu Gly Trp Ser Gly Pro His Gly Ala Leu Leu
            20                  25                  30

Gly His Ser Leu Val Ser Pro Thr Leu Ser Ile Ser Ser Asp Ser Ser
        35                  40                  45

Pro Ala Ser Tyr Ser Pro Ala Ala Leu Leu Leu Gly Thr Ser Leu
    50                  55                  60

Pro Lys Phe Thr Trp Arg Glu Gly Gln Lys Gln Leu Pro Leu Ile Gly
65                  70                  75                  80

Cys Val Leu Leu Leu Ile Ala Leu Val Val Ser Leu Ile Ile Leu Phe
                85                  90                  95

Gln Phe Trp Gln Gly His Thr Gly Ile Arg Tyr Lys Glu Gln Arg Glu
            100                 105                 110

Ser Cys Pro Lys His Ala Val Arg Cys Asp Gly Val Val Asp Cys Lys
        115                 120                 125

Leu Lys Ser Asp Glu Leu Gly Cys Val Arg Phe Asp Trp Asp Lys Ser
    130                 135                 140

Leu Leu Lys Ile Tyr Ser Gly Ser Ser His Gln Trp Leu Pro Ile Cys
145                 150                 155                 160

Ser Ser Asn Trp Asn Asp Ser Tyr Ser Glu Lys Thr Cys Gln Gln Leu
                165                 170                 175

Gly Phe Glu Ser Ala His Arg Thr Thr Glu Val Ala His Arg Asp Phe
            180                 185                 190

Ala Asn Ser Phe Ser Ile Leu Arg Tyr Asn Ser Thr Ile Gln Glu Ser
        195                 200                 205

Leu His Arg Ser Glu Cys Pro Ser Gln Arg Tyr Ile Ser Leu Gln Cys
    210                 215                 220

Ser His Cys Gly Leu Arg Ala Met Thr Gly Arg Ile Val Gly Gly Ala
225                 230                 235                 240

Leu Ala Ser Asp Ser Lys Trp Pro Trp Gln Val Ser Leu His Phe Gly
                245                 250                 255

Thr Thr His Ile Cys Gly Gly Thr Leu Ile Asp Ala Gln Trp Val Leu
            260                 265                 270

Thr Ala Ala His Cys Phe Phe Val Thr Arg Glu Lys Val Leu Glu Gly
        275                 280                 285
```

```
Trp Lys Val Tyr Ala Gly Thr Ser Asn Leu His Gln Leu Pro Glu Ala
    290                 295                 300

Ala Ser Ile Ala Glu Ile Ile Asn Ser Asn Tyr Thr Asp Glu Glu
305                 310                 315                 320

Asp Asp Tyr Asp Ile Ala Leu Met Arg Leu Ser Lys Pro Leu Thr Leu
                325                 330                 335

Ser Ala His Ile His Pro Ala Cys Leu Pro Met His Gly Gln Thr Phe
            340                 345                 350

Ser Leu Asn Glu Thr Cys Trp Ile Thr Gly Phe Gly Lys Thr Arg Glu
        355                 360                 365

Thr Asp Asp Lys Thr Ser Pro Phe Leu Arg Glu Val Gln Val Asn Leu
    370                 375                 380

Ile Asp Phe Lys Lys Cys Asn Asp Tyr Leu Val Tyr Asp Ser Tyr Leu
385                 390                 395                 400

Thr Pro Arg Met Met Cys Ala Gly Asp Leu Arg Gly Gly Arg Asp Ser
                405                 410                 415

Cys Gln Gly Asp Ser Gly Gly Pro Leu Val Cys Glu Gln Asn Asn Arg
            420                 425                 430

Trp Tyr Leu Ala Gly Val Thr Ser Trp Gly Thr Gly Cys Gly Gln Arg
        435                 440                 445

Asn Lys Pro Gly Val Tyr Thr Lys Val Thr Glu Val Leu Pro Trp Ile
    450                 455                 460

Tyr Ser Lys Met Glu Ser Glu Val Arg Phe Arg Lys Ser
465                 470                 475

<210> SEQ ID NO 3
<211> LENGTH: 1341
<212> TYPE: DNA
<213> ORGANISM: Homo sapiens
<220> FEATURE:
<221> NAME/KEY: CDS
<222> LOCATION: (1)..(1341)
<223> OTHER INFORMATION:

<400> SEQUENCE: 3 atg gga caa aat tca ttc att cat tca att gac ttt gag ccc cat aaa    48
Met Gly Gln Asn Ser Phe Ile His Ser Ile Asp Phe Glu Pro His Lys
1               5                   10                  15 atc tca ttc caa ctt ctg ggg tgg agt ggt cct cac ggg gcc ctc ctg    96
Ile Ser Phe Gln Leu Leu Gly Trp Ser Gly Pro His Gly Ala Leu Leu
            20                  25                  30 ggc cac agt ctt gtt tcc ccc acc ctc tcc atc tcg tcg gac tcc tct   144
Gly His Ser Leu Val Ser Pro Thr Leu Ser Ile Ser Ser Asp Ser Ser
        35                  40                  45 cca gcc tca tat tcc cct gct gcc gcc ctg ctc cta ggt acg agc ctg   192
Pro Ala Ser Tyr Ser Pro Ala Ala Ala Leu Leu Leu Gly Thr Ser Leu
    50                  55                  60 ccc aag ttc acc tgg cgg gag ggc cag aag cag cta ccg ctc atc ggg   240
Pro Lys Phe Thr Trp Arg Glu Gly Gln Lys Gln Leu Pro Leu Ile Gly
65                  70                  75                  80 tgc gtg ctc ctc ctc att gcc ctg gtg gtt tcg ctc atc atc ctc ttc   288
Cys Val Leu Leu Leu Ile Ala Leu Val Val Ser Leu Ile Ile Leu Phe
                85                  90                  95 cag ttc tgg cag ggc cac aca ggg atc agg tac aag gag cag agg gag   336
Gln Phe Trp Gln Gly His Thr Gly Ile Arg Tyr Lys Glu Gln Arg Glu
            100                 105                 110 agc tgt ccc aag cac gct gtt cgc tgt gac ggg gtg gtg gac tgc aag   384
Ser Cys Pro Lys His Ala Val Arg Cys Asp Gly Val Val Asp Cys Lys
        115                 120                 125
```

-continued

| | |
|---|---|
| ctg aag agt gac gag ctg ggc tgc gtg agg ttt gac tgg gac aag tct<br>Leu Lys Ser Asp Glu Leu Gly Cys Val Arg Phe Asp Trp Asp Lys Ser<br>130                        135                    140 | 432 |
| ctg ctt aaa atc tac tct ggg tcc tcc cat cag tgg ctt ccc atc tgt<br>Leu Leu Lys Ile Tyr Ser Gly Ser Ser His Gln Trp Leu Pro Ile Cys<br>145                      150                    155                    160 | 480 |
| agc agc aac tgg aat gac tcc tac tca gag aag acc tgc cag cag ctg<br>Ser Ser Asn Trp Asn Asp Ser Tyr Ser Glu Lys Thr Cys Gln Gln Leu<br>              165                    170                    175 | 528 |
| ggt ttc gag agg tct gaa tgc cct tcc cag cgg tat atc tcc ctc cag<br>Gly Phe Glu Arg Ser Glu Cys Pro Ser Gln Arg Tyr Ile Ser Leu Gln<br>        180                    185                    190 | 576 |
| tgt tcc cac tgc gga ctg agg gcc atg acc ggg cgg atc gtg gga ggg<br>Cys Ser His Cys Gly Leu Arg Ala Met Thr Gly Arg Ile Val Gly Gly<br>            195                    200                    205 | 624 |
| gcg ctg gcc tcg gat agc aag tgg cct tgg caa gtg agt ctg cac ttc<br>Ala Leu Ala Ser Asp Ser Lys Trp Pro Trp Gln Val Ser Leu His Phe<br>210                        215                    220 | 672 |
| ggc acc acc cac atc tgt gga ggc acg ctc att gac gcc cag tgg gtg<br>Gly Thr Thr His Ile Cys Gly Gly Thr Leu Ile Asp Ala Gln Trp Val<br>225                        230                    235                    240 | 720 |
| ctc act gcc gcc cac tgc ttc ttc gtg acc cgg gag aag gtc ctg gag<br>Leu Thr Ala Ala His Cys Phe Phe Val Thr Arg Glu Lys Val Leu Glu<br>                  245                    250                    255 | 768 |
| ggc tgg aag gtg tac gcg ggc acc agc aac ctg cac cag ttg cct gag<br>Gly Trp Lys Val Tyr Ala Gly Thr Ser Asn Leu His Gln Leu Pro Glu<br>        260                    265                    270 | 816 |
| gca gcc tcc att gcc gag atc atc atc aac agc aat tac acc gat gag<br>Ala Ala Ser Ile Ala Glu Ile Ile Ile Asn Ser Asn Tyr Thr Asp Glu<br>275                        280                    285 | 864 |
| gag gac gac tat gac atc gcc ctc atg cgg ctg tcc aag ccc ctg acc<br>Glu Asp Asp Tyr Asp Ile Ala Leu Met Arg Leu Ser Lys Pro Leu Thr<br>            290                    295                    300 | 912 |
| ctg tcc gct cac atc cac cct gct tgc ctc ccc atg cat gga cag acc<br>Leu Ser Ala His Ile His Pro Ala Cys Leu Pro Met His Gly Gln Thr<br>305                        310                    315                    320 | 960 |
| ttt agc ctc aat gag acc tgc tgg atc aca ggc ttt ggc aag acc agg<br>Phe Ser Leu Asn Glu Thr Cys Trp Ile Thr Gly Phe Gly Lys Thr Arg<br>                  325                    330                    335 | 1008 |
| gag aca gat gac aag aca tcc ccc ttc ctc cgg gag gtg cag gtc aat<br>Glu Thr Asp Asp Lys Thr Ser Pro Phe Leu Arg Glu Val Gln Val Asn<br>        340                    345                    350 | 1056 |
| ctc atc gac ttc aag aaa tgc aat gac tac ttg gtc tat gac agt tac<br>Leu Ile Asp Phe Lys Lys Cys Asn Asp Tyr Leu Val Tyr Asp Ser Tyr<br>            355                    360                    365 | 1104 |
| ctt acc cca agg atg atg tgt gct ggg gac ctt cgt ggg ggc aga gac<br>Leu Thr Pro Arg Met Met Cys Ala Gly Asp Leu Arg Gly Gly Arg Asp<br>370                        375                    380 | 1152 |
| tcc tgc cag gga gac agc ggg ggg cct ctt gtc tgt gag cag aac aac<br>Ser Cys Gln Gly Asp Ser Gly Gly Pro Leu Val Cys Glu Gln Asn Asn<br>385                        390                    395                    400 | 1200 |
| cgc tgg tac ctg gca ggt gtc acc agc tgg ggc aca ggc tgt ggc cag<br>Arg Trp Tyr Leu Ala Gly Val Thr Ser Trp Gly Thr Gly Cys Gly Gln<br>                  405                    410                    415 | 1248 |
| aga aac aaa cct ggt gtg tac acc aaa gtg aca gaa gtt ctt ccc tgg<br>Arg Asn Lys Pro Gly Val Tyr Thr Lys Val Thr Glu Val Leu Pro Trp<br>        420                    425                    430 | 1296 |
| att tac agc aag atg gag agc gag gtg cga ttc aga aaa tcc taa<br>Ile Tyr Ser Lys Met Glu Ser Glu Val Arg Phe Arg Lys Ser | 1341 |

435        440        445

<210> SEQ ID NO 4
<211> LENGTH: 446
<212> TYPE: PRT
<213> ORGANISM: Homo sapiens

<400> SEQUENCE: 4

```
Met Gly Gln Asn Ser Phe Ile His Ser Ile Asp Phe Glu Pro His Lys
 1               5                  10                  15

Ile Ser Phe Gln Leu Leu Gly Trp Ser Gly Pro His Gly Ala Leu Leu
            20                  25                  30

Gly His Ser Leu Val Ser Pro Thr Leu Ser Ile Ser Ser Asp Ser Ser
        35                  40                  45

Pro Ala Ser Tyr Ser Pro Ala Ala Leu Leu Gly Thr Ser Leu
 50                  55                  60

Pro Lys Phe Thr Trp Arg Glu Gly Gln Lys Gln Leu Pro Leu Ile Gly
 65                  70                  75                  80

Cys Val Leu Leu Leu Ile Ala Leu Val Val Ser Leu Ile Ile Leu Phe
                 85                  90                  95

Gln Phe Trp Gln Gly His Thr Gly Ile Arg Tyr Lys Glu Gln Arg Glu
                100                 105                 110

Ser Cys Pro Lys His Ala Val Arg Cys Asp Gly Val Val Asp Cys Lys
            115                 120                 125

Leu Lys Ser Asp Glu Leu Gly Cys Val Arg Phe Asp Trp Asp Lys Ser
130                 135                 140

Leu Leu Lys Ile Tyr Ser Gly Ser His Gln Trp Leu Pro Ile Cys
145                 150                 155                 160

Ser Ser Asn Trp Asn Asp Ser Tyr Ser Glu Lys Thr Cys Gln Gln Leu
                165                 170                 175

Gly Phe Glu Arg Ser Glu Cys Pro Ser Gln Arg Tyr Ile Ser Leu Gln
            180                 185                 190

Cys Ser His Cys Gly Leu Arg Ala Met Thr Gly Arg Ile Val Gly Gly
        195                 200                 205

Ala Leu Ala Ser Asp Ser Lys Trp Pro Trp Gln Val Ser Leu His Phe
210                 215                 220

Gly Thr Thr His Ile Cys Gly Gly Thr Leu Ile Asp Ala Gln Trp Val
225                 230                 235                 240

Leu Thr Ala Ala His Cys Phe Phe Val Thr Arg Glu Lys Val Leu Glu
                245                 250                 255

Gly Trp Lys Val Tyr Ala Gly Thr Ser Asn Leu His Gln Leu Pro Glu
            260                 265                 270

Ala Ala Ser Ile Ala Glu Ile Ile Asn Ser Asn Tyr Thr Asp Glu
        275                 280                 285

Glu Asp Asp Tyr Asp Ile Ala Leu Met Arg Leu Ser Lys Pro Leu Thr
    290                 295                 300

Leu Ser Ala His Ile His Pro Ala Cys Leu Pro Met His Gly Gln Thr
305                 310                 315                 320

Phe Ser Leu Asn Glu Thr Cys Trp Ile Thr Gly Phe Gly Lys Thr Arg
                325                 330                 335

Glu Thr Asp Asp Lys Thr Ser Pro Phe Leu Arg Glu Val Gln Val Asn
            340                 345                 350

Leu Ile Asp Phe Lys Lys Cys Asn Asp Tyr Leu Val Tyr Asp Ser Tyr
        355                 360                 365
```

```
Leu Thr Pro Arg Met Met Cys Ala Gly Asp Leu Arg Gly Gly Arg Asp
        370                 375                 380

Ser Cys Gln Gly Asp Ser Gly Gly Pro Leu Val Cys Glu Gln Asn Asn
385                 390                 395                 400

Arg Trp Tyr Leu Ala Gly Val Thr Ser Trp Gly Thr Gly Cys Gly Gln
            405                 410                 415

Arg Asn Lys Pro Gly Val Tyr Thr Lys Val Thr Glu Val Leu Pro Trp
                420                 425                 430

Ile Tyr Ser Lys Met Glu Ser Glu Val Arg Phe Arg Lys Ser
            435                 440                 445

<210> SEQ ID NO 5
<211> LENGTH: 8
<212> TYPE: PRT
<213> ORGANISM: Artificial sequence
<220> FEATURE:
<223> OTHER INFORMATION: FLAG peptide

<400> SEQUENCE: 5

Asp Tyr Lys Asp Asp Asp Asp Lys
1               5

<210> SEQ ID NO 6
<211> LENGTH: 418
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (1)..(418)
<223> OTHER INFORMATION: Xaa = unknown

<400> SEQUENCE: 6

Ser Cys Ile Pro Xaa Ser Xaa Trp Cys Asp Gly Val Xaa Asp Cys Pro
1               5                   10                  15

Xaa Gly Glu Asp Glu Xaa Xaa Cys Val Xaa Xaa Xaa Xaa Gly Pro
            20                  25                  30

Xaa Xaa Xaa Val Arg Leu Tyr Gly Asp Xaa Xaa Leu Leu Gln Val Tyr
            35                  40                  45

Ser Ser Xaa Xaa Xaa Trp Xaa Pro Val Cys Ser Asp Asn Trp Asn
50                  55                  60

Glu Ser Tyr Ser Xaa Xaa Ala Cys Xaa Gln Met Gly Xaa Xaa Ser Ala
65                  70                  75                  80

Xaa Tyr Xaa Ser Glu Xaa Gly Xaa Xaa Xaa Arg Xaa Gly Ala Asn Ser
            85                  90                  95

Phe Xaa Lys Leu Asn Val Ser Pro Xaa Asn Leu Leu Xaa Xaa Asp Xaa
            100                 105                 110

Tyr Thr Ser Xaa Ile Gln Xaa Xaa Leu Xaa Arg Ser Ser Xaa Xaa
            115                 120                 125

Cys Pro Ser Gly Xaa Val Val Ser Leu Gln Cys Ser Xaa Gln Asp Cys
130                 135                 140

Gly Val Arg Leu Asn Ala Xaa Xaa Met Thr Ser Arg Ile Val Gly Gly
145                 150                 155                 160

Xaa Xaa Ala Ser Xaa Gly Xaa Trp Pro Trp Gln Val Ser Leu Gln Xaa
            165                 170                 175

Xaa Xaa Gly Val His Leu Cys Gly Gly Ser Leu Ile Xaa Pro Xaa Trp
            180                 185                 190

Val Leu Thr Ala Ala His Cys Val Xaa Gly Arg Xaa Xaa Lys Pro Leu
```

-continued

```
                195                 200                 205
Xaa Gly Trp Xaa Val Phe Ala Gly Ile Leu Thr Xaa Ser Leu His Xaa
    210                 215                 220

Xaa Pro Xaa Ala Xaa Xaa Arg Xaa Val Glu Lys Ile Ile Ile His Pro
225                 230                 235                 240

Asn Tyr Xaa Xaa Xaa Xaa Xaa Xaa Ser Xaa Xaa Lys Asp Asn Asp
                245                 250                 255

Ile Ala Leu Met Lys Leu Ser Lys Pro Leu Thr Phe Xaa Asp Tyr Ile
            260                 265                 270

Gln Pro Val Cys Leu Pro Asn Pro Gly Gln Xaa Leu Xaa Pro Gly Thr
        275                 280                 285

Thr Cys Trp Ile Xaa Gly Trp Gly Ala Thr Xaa Glu Xaa Xaa Gly Lys
    290                 295                 300

Thr Ser Pro Val Leu Gln Glu Ala Xaa Val Pro Leu Ile Asp Asn Lys
305                 310                 315                 320

Xaa Cys Asn Ser Tyr Xaa Val Tyr Asp Asn Xaa Ile Thr Pro Arg Met
                325                 330                 335

Ile Cys Ala Gly Tyr Leu Glu Gly Gly Val Asp Ser Cys Gln Gly Asp
            340                 345                 350

Ser Gly Gly Pro Leu Val Cys Glu Xaa Xaa Xaa Xaa Gln Asn Asn Arg
        355                 360                 365

Trp Trp Leu Xaa Gly Xaa Thr Ser Trp Gly Xaa Gly Cys Xaa Ala Lys
    370                 375                 380

Ala Asn Lys Pro Gly Val Tyr Thr Xaa Val Thr Xaa Phe Leu Xaa Trp
385                 390                 395                 400

Ile Tyr Ser Gln Met Xaa Ala Glu Xaa Arg Phe Arg Lys Ser Xaa Xaa
                405                 410                 415

Xaa Xaa
```

DENDRITIC CELL TRANSMEMBRANE SERINE PROTEASE

This application claims the benefit of priority to provisional application 60/299,606, filed Jun. 20, 2001.

FIELD OF THE INVENTION

This invention relates to Dendritic Cell Transmembrane Serine Protease (DCTSP), a new member of the Type II Transmembrane Serine Protease polypeptide family, and to methods of making and using DCTSP polypeptides.

BACKGROUND OF THE INVENTION

Type II Transmembrane Serine Protease (TTSP) polypeptides are related, membrane-anchored polypeptides that are involved in cell surface proteolysis and share common structural features including a proteolytic domain, a stem region comprising varying modular structural domains, a transmembrane domain, and a short cytoplasmic domain (Hooper et al., J. Biol. Chem. 276:857, 2001). Members of this family include hepsin (Leytus et al., Biochemistry 27:1067, 1988), enteropeptidase (also referred to as enterokinase; Kitamoto et al., Biochemistry 34:4562, 1995), TMPRSS2 (Paoloni-Giacobino et al., Genomics 44:309 1997), human airway trypsin-like protease (HAT; Yamaoka et al., J. Biol Chem. 273:11895, 1998), corin (Yan et al. J. Biol. Chem. 274:14296, 1999), MT-SP1 (also known as matriptase; Lin et al., J. Biol. Chem. 274:18231, 1999), and TMPRSS4 (Wallrapp et al., Cancer Res. 60:2602, 2000). Kim et al. (Biochim. Biophys. Acta. 1518:204, 2001) disclose cDNAs encoding proteins with putative serine protease domains and potential regulatory domains; one of the putative proteins also had a transmembrane domain.

The proteolytic domains of TTSPs exhibit a high degree of homology, with highly conserved motifs comprising histidine, aspartate and serine residues thought to be necessary for catalytic activity. A conserved activation motif contains an arginine or lysine, and indicates that the TTSPs are likely to be activated following cleavage. The presence of conserved cysteine residues, and their predicted disulphide bonding pattern, provide support for the belief that TTSPs are likely to remain associated with the cell membrane even after cleavage/activation, although soluble forms of some TTSPs have been identified (Hooper et al., supra). Additional conserved cysteine residues appear to be involved in forming disulphide bonds within the catalytic domain. Cleavage specificities and potential substrates have been identified for some TTSPs, but remain unknown for most; it is likely that the substrate(s) for TTSPs preferentially contain an arginine or lysine in the P1 amino acid position (as originally described for serine proteases in Schecter et al., Biochem. Biophys. Res. Commun. 27:157, 1967).

A hydrophobic, transmembrane domain is present near the N-terminus of the members of the TTSP family, indicating that the proteolytic domain is extracellular. The presence of the catalytic domain on the outside of cell, but presumably still in association with the cell membrane, suggests a role for this family of serine proteases in regulated release of substrate proteins from the cell surface, either from the same cell upon which the TTSP is found or from a cell that is in close association with such a cell.

Most TTSPs exhibit relatively restricted expression patterns, indicating that they may carry out tissue-specific functions (Hooper et al., supra). The variability of the length of the cytoplasmic domains of TTSPs renders it difficult to predict a role for these proteins in cellular signaling; however, some TTSPs do contain consensus phosphorylation sites within the cytoplasmic domain. The greatest degree of variability between members of the TTSP family occurs in the stem region, which may contain up to eleven structural domains. The variety in number and type of structural domains present in the stem region suggests that it may serve to regulate the activity and/or binding of TTSPs to substrates. The role of cell surface proteolysis in homeostasis and disease demonstrates that there is a need in the art to identify and characterize additional members of the TTSP family.

SUMMARY OF THE INVENTION

The present invention provides a novel serine protease, referred to as human Dendritic Cell Transmembrane Serine Protease (DCTSP), a Type II transmembrane protein depicted in SEQ ID NOs:1 and 2; a splice variant having 446 amino acids was also isolated; the nucleotide and amino acid sequence of this variant are shown in SEQ ID NOs:3 and 4. Also provided are DCTSP polypeptides that are encoded by nucleic acids capable of hybridizing to the DNAs of SEQ ID NOs:1 or 3 and that have at least one DCTSP activity, DCTSP polypeptides that are at least 80% identical to the DCTSP polypeptides of SEQ ID NOs: 2 or 4 and that have at least one DCTSP activity, and fragments of such DCTSP polypeptides that have at least one DCTSP activity.

The invention further provides various forms of DCTSP, including: a protein comprising amino acids x to y of SEQ ID NO:2, wherein x represents an integer from 1 to 47, inclusive, and y represents an integer from 470 to 477, inclusive; a protein comprising amino acids x to y of SEQ ID NO:2, wherein x represents an integer from 91 to 96, inclusive, and y represents an integer from 470 to 477, inclusive; a protein comprising amino acids x to y of SEQ ID NO:2, wherein x represents an integer from 207 to 212, inclusive, and y represents an integer from 470 to 477, inclusive; a protein comprising amino acids x to y of SEQ ID NO:2, wherein x represents an integer from 91 to 96, inclusive, and y represents an integer from 221 to 226, inclusive; a protein comprising amino acids x to y of SEQ ID NO:2, wherein x represents an integer from 1 to 47, inclusive, and y represents an integer from 75 to 95, inclusive; a protein comprising amino acids x to y of SEQ ID NO:4, wherein x represents an integer from 1 to 47, inclusive, and y represents an integer from 441 to 446, inclusive; a protein comprising amino acids x to y of SEQ ID NO:4, wherein x represents an integer from 91 to 96, inclusive, and y represents an integer from 441 to 446, inclusive; a protein comprising amino acids x to y of SEQ ID NO:4, wherein x represents an integer from 174 to 179, inclusive, and y represents an integer from 441 to 446, inclusive; a protein comprising amino acids x to y of SEQ ID NO:4, wherein x represents an integer from 174 to 179, inclusive, and y represents an integer from 190 to 195, inclusive; and a protein comprising amino acids x to y of SEQ ID NO:4, wherein x represents an integer from 91 to 96, inclusive, and y represents an integer from 190 to 195, inclusive. Also comprehended herein are nucleic acids encoding the aforementioned DCTSP polypeptides, vectors comprising such nucleic acids, host cells transformed or transfected with such vectors (including hosts cells wherein the DNA encoding a DCTSP polypeptide is integrated into host cell chromosomal DNA), and processes for obtaining DCTSP polypeptides by culturing such host cells.

Soluble forms of DCTSP (including fragments comprising the extracellular domain as well as fragments comprising the cytoplasmic domain) will be useful in vitro to screen for agonists or antagonists of DCTSP activity utilizing one or more screening methods, which methods also form an aspect of the present invention. In one aspect, the inventive methods utilize homogeneous assay formats such as fluorescence resonance energy transfer, fluorescence polarization, time-resolved fluorescence resonance energy transfer, scintillation proximity assays, reporter gene assays, fluorescence quenched enzyme substrate, chromogenic enzyme substrate and electrochemiluminescence. In another aspect, the inventive methods utilize heterogeneous assay formats such as enzyme-linked immunosorbant assays (ELISA) or radioimmunoassays. In yet another aspect of the invention are cell-based assays, for example those utilizing reporter genes, as well as functional assays that analyze the effect of an antagonist or agonist on biological function(s).

The invention further provides methods for producing information comprising the identity of a compound that alters one or more activities of DCTSP, comprising using one or more of the inventive assays to identify a compound or compounds that alter the binding and/or cleavage of substrate by DCTSP. In one embodiment, the compound increases (or agonizes) the binding and/or cleavage of substrate, and in another distinct embodiment, the compound decreases (or antagonizes) the binding and/or cleavage of substrate.

Also provided by the invention is the information produced according to the inventive methods, said information comprising the identity of a compound that alters the activity of DCTSP, and preferably embodied in a storage medium selected from the group consisting of paper, magnetic tape, optical tape, floppy disks, compact disks, computer system hard drives, and computer memory units. In a further aspect, the invention provides a database comprising said information, wherein the information is preferably embodied in a computer-readable medium, and a separate embodiment wherein the information is embodied in a human-readable medium.

Additionally provided by the invention is a computer system comprising a database containing records pertaining to a plurality of compounds, wherein the records comprise results of an assay of the invention, and a user interface allowing a user to access information regarding the plurality of compounds. In another aspect of the invention, a computer system is provided for storing and retrieving data on a plurality of compounds, the computer system comprising:

input means for entering data for the compounds into a storage medium;

a processor for creating an individual record for each compound, the processor assigning specific identifying values for each compound;

means for selecting one or more of the records based on results in an assay; and means for transmitting information in the record or records to an output device to produce a report; preferably a report in human-readable form, and wherein the computer system preferably further comprises a video display unit.

The invention also provides a method of using the computer system of the invention to select one or more compounds for testing from a plurality of compounds having records stored in a database, the method comprising: displaying a list of said records or a field for entering information identifying one or more of said records; and selecting one or more of the records from the list or the record or records identified by entering information in the field.

Further, the invention provides a method of operating a computer system for analyzing compounds that modulate the activity of DCTSP, the method comprising:

entering data relating to a plurality of compounds into a storage medium;

processing the data to create an individual record for each compound;

testing compounds for the ability to modulate activity of DCTSP; and communicating results from the testing into the storage medium such that results for each compound are associated with the individual record for that compound; wherein in one embodiment the storage medium comprises one or more computer memory units, and in another embodiment the computer system further comprises a video display unit.

In yet another aspect of the invention, a database is provided comprising records generated according to the methods of the invention, and a method is provided for selecting compounds that modulate the activity of DCTSP, comprising compiling said database, analyzing the testing results, and selecting one or more compounds.

BRIEF DESCRIPTION OF THE DRAWINGS

FIG. 1 represents an alignment between DCTSP and human chymotrypsin. Conserved Cys residues are shown in bold face; the catalytic triad (HDS) is underlined. The relevant amino acid residue numbers are shown immediately above the amino acid sequence for chymotrypsin, and immediately below the amino acid sequence for DCTSP. Amino acid identity is indicated by an asterisk (*). Chymotrypsin disulfide bonding cysteines are 1–122, 42–58, 136–201, and 191–220; based on homology, predicted DCTSP disulfide bonding cysteines are 227–344, 261–277, 358–427, 390–406, and 417–445. DCTSP contains four predicted N-linked glycosylation sites, at Asn165, Asn202, Asn315 and Asn355.

DETAILED DESCRIPTION OF THE INVENTION

A novel Type II Transmembrane Serine Protease (TTSP) polypeptide having structural features characteristic of this polypeptide family has been identified; the nucleotide and translated amino acid sequence is provided in SEQ ID NO:1; a splice variant was also identified, and the nucleotide and translated amino acid sequence thereof are given in SEQ ID NO:3. The polypeptide is referred to as Dendritic Cell Transmembrane Serine Protease (DCTSP). PCR amplification from tissue-specific cDNA libraries indicated that DCTSP transcripts are present in immunologically-important tissues (spleen, lymph node, tonsil, peripheral blood leukocytes), as well as in fetal lung and placenta. DCTSP transcripts are also present in cells of epithelial origin, including lung, trachea, and skin. The gene encoding DCTSP is located on human chromosome 11, near the junction between 11q23 and 11q24; probes derived from the DNA of SEQ ID NOs:1 and 3 (or a fragment thereof) can be used to detect the presence of chromosome #11 in a sample. Such probes are also useful for the genomic mapping of human heritable disorders that have been genetically mapped to this region, including exudative familial vitreoretinopathy, Tourette syndrome, Jacobsen syndrome, immunodeficiency associated with the delta and/or epsilon subunits of the T cell receptor, autosomal recessive benign erythrocytosis, breast cancer-3 (BRCA-3), non-small cell lung cancer, hydrolethalus syndrome, acute myeloid leukemia, and primary hypoalphalipoproteinemia.

The typical structural elements common to members of the TTSP polypeptide family include an intracellular domain, a transmembrane region, a stem region, and a catalytic domain. The stem region of the various members of the TTSP family varies in length, and in the number and/or type of structural domains; see Hooper et al., supra, for a review of the various family members and the types of structural domains identified therein. The catalytic domain exhibits a characteristic triad of amino acids, characterized in the chymotrypsin active site and being made up of His57, Asp102 and Ser195 of that enzyme (Perona and Craik, *J. Biol. Chem.* 272:29987, 1997). The skilled artisan will recognize that the boundaries of the regions of the DCTSP polypeptides described above are approximate and that the precise boundaries of such domains, as for example the boundaries of the transmembrane region (which can be predicted by using computer programs available for that purpose), can vary from those predicted.

DCTSP is a transmembrane protein having 477 amino acid residues; amino acids 1 through 75 are predicted to form an intracellular domain, followed by a transmembrane region (amino acids 76 to 96), while amino acids 97 through 477 form an extracellular domain (the protease domain is from amino acid 227 to 477). A splice variant having 446 amino acids (SEQ ID NOs:3 and 4) was also isolated; this variant appears to have a deletion of 31 amino acids (amino acids 180 through 210 of SEQ ID NO:2) in the extracellular region, prior to the catalytic domain. The catalytic triad in DCTSP is formed by His276, Asp324 and Ser421 of SEQ ID NO:2. Amino acids 235 through 239 represent a potential activation site for the DCTSP of SEQ ID NO:1; this corresponds to amino acids 204 through 208 of SEQ ID NO:3. An alignment showing the sequence similarities between the extracellular domain of the DCTSP of SEQ ID NO:2 and a consensus TTSP extracellular domain is presented in Table 2 herein.

A shed, soluble version of DCTSP may be generated by proteolytic cleavage at or near the transmembrane region, similar to the shedding of many of receptors and other membrane proteins that are also found in soluble form. Alternatively, a soluble form of DCTSP can be prepared by expression of a nucleic acid encoding the extracellular domain or a portion thereof.

The binding pocket of a serine protease is defined by specific residues that dictate what substrate(s) can bind and be cleaved by the protease. Using the nomenclature first suggested by: Schechter and Berger (*Biochem. Biophys. Res. Commun.* 27:157, 1968), sites in the protease are referred to as "S-sites," (S1, S2 etc.) with the first S site, designated S1, being the site in the binding pocket that is occupied by the residue in the substrate that will be cleaved (referred to as P1). On the other side of the cleavage (and binding pocket site) the residues are referred to as S1', S2' or P1', P2' etc. Proteolytic cleavage occurs between P1 and P1' of the substrate. A diagram illustrating this is shown in Table 1 below.

TABLE 1

Diagram of Substrate Binding Pocket Residues
and Residues in the Substrate that Interact Therewith

| | |
|---|---|
| Protease binding pocket: | S4 S3 S2 S1-S1' S2' S3' S4' |
| Substrate residues in the binding pocket: | P4 P3 P2 P1-P1' P2' P3' P4' | cleavage site

The S1 site of a serine protease dictates what the substrate P1 residue will be; in the case of DCTSP the S1 residue is Asp415 (equivalent to Ser189 in chymotrypsin; see Perona and Craik, supra, FIG. 1), indicating that the P1 site in the binding pocket will accept a basic residue (Arg or Lys) at P1 of the substrate. DCTSP and related family members have an equivalent Asp at this site, and thus will likely cleave at an Arg or Lys residue (so called trypsin-like activity). Two other binding pocket residues are the S2 site which is Ser440 (equivalent to chymotrypsin Ser214) and the S3 site which is Gly442 (equivalent to chymotrypsin Gly216).

Typical activities or functions associated with DCTSP polypeptides include binding substrate(s), binding antibodies that are immunologically reactive with DCTSP, and proteolytic hydrolysis of peptide bonds. DCTSP polypeptides having serine protease activity bind proteins and hydrolyze specific peptide bonds therein to yield fragmented proteins and/or peptides. Such proteolytic processing plays an important role in a number of biological systems, including the hydrolysis of proinsulin to form insulin, the activation of various proteolytic enzymes themselves, and the processing of proteins involved in activities as diverse as blood coagulation, wound healing, apoptosis, and the immune response. Activities of a DCTSP cytoplasmic domain may include interacting with cytoskeletal components and/or signaling molecules.

The protease activity is associated with the catalytic domain of DCTSP polypeptides. Thus, for uses requiring protease activity, preferred DCTSP polypeptides include those having the catalytic domain. Preferred DCTSP polypeptides further include oligomers or fusion polypeptides comprising at least one catalytic portion of one or more DCTSP polypeptides, and fragments of any of these polypeptides that have serine protease activity. The protease activity of DCTSP polypeptides can be determined, for example, in one or more protease assays that are known in the art (for example, those described in *Handbook of Proteolytic Enzymes*, edited by Alan J. Barrett, Neil D. Rawlings and J. Fred Woesner; published by Academic Press, 1998.

DNAs, Proteins and Analogs

The present invention provides isolated DCTSP polypeptides and analogs (or muteins) thereof having an activity exhibited by the native molecule (i.e., DCTSP muteins that exhibit serine protease activity, or bind to DCTSP-specific antibodies). Such proteins are substantially free of contaminating endogenous materials and, optionally, without associated native-pattern glycosylation. Derivatives of DCTSP within the scope of the invention also include various structural forms of the primary protein which retain biological activity. Due to the presence of ionizable amino and carboxyl groups, for example, a DCTSP protein may be in the form of acidic or basic salts, or may be in neutral form. Individual amino acid residues may also be modified by oxidation, reduction, or isomerization. The primary amino acid structure may be modified by forming covalent or aggregative conjugates with other chemical moieties, such as glycosyl groups, lipids, phosphate, acetyl groups and the like, or by creating amino acid sequence mutants. Covalent derivatives are prepared by linking particular functional groups to amino acid side chains or at the N- or C-termini.

Derivatives of DCTSP may also be obtained by the action of cross-linking agents, such as M-maleimidobenzoyl succinimide ester and N-hydroxysuccinimide, at cysteine and lysine residues. The inventive proteins may also be covalently bound through reactive side groups to various insoluble resins or matrices, such as cyanogen bromide-activated, bisoxirane-activated, carbonyldiimidazole-activated or tosyl-activated agarose structures, or by adsorbing to polyolefin surfaces (with or without glutaraldehyde cross-linking). Once bound to a matrix (or resin), the proteins may be used to selectively bind (for purposes of assay or purification) antibodies raised against the proteins or against other proteins that are similar to DCTSP, as well as other proteins that bind DCTSP or homologs thereof.

Soluble forms of DCTSP are also within the scope of the invention. The nucleotide and predicted amino acid sequence of the full-length human DCTSP are shown in SEQ ID NOs:1 and 2; the nucleotide and amino acid sequence of a splice variant are shown in SEQ ID NOs:3 and 4. The intracellular domain of DCTSP (amino acids 1 through 75) is predicted to be followed by a transmembrane domain (amino acids 76 through 96), a stem region (amino acids 97 through 226) and a catalytic domain (amino acids 227 through 477).

Soluble DCTSP comprises the extracellular domain or a fragment thereof. Fragments can be prepared using known techniques to isolate a desired portion of the extracellular region, and can be prepared, for example, by comparing the extracellular region with those of other members of the TTSP and selecting forms similar to those prepared for other family members. Alternatively, unique restriction sites or PCR techniques that are known in the art can be used to prepare numerous truncated forms which can be expressed and analyzed for activity. In addition, expression of a splice variant comprised of the stem region and catalytic domain only could also result in a soluble form of DCTSP.

Other derivatives of the DCTSP proteins within the scope of this invention include covalent or aggregative conjugates of the proteins or their fragments with other peptides or polypeptides, such as by synthesis in recombinant culture as N-terminal or C-terminal fusions. For example, the polypeptide may comprise a signal (or leader) polypeptide sequence at the N-terminal region of the protein which co-translationally or post-translationally directs transfer of the protein from the site of synthesis to a site inside or outside of the cell membrane or wall (e.g., the yeast alpha-factor leader).

Protein fusions can comprise peptides added to facilitate purification or identification (referred to as 'tags') of DCTSP proteins and homologs (e.g., poly-His). One such tag peptide is the FLAG® peptide (DYKDDDDK; SEQ ID NO:5), which is highly antigenic and provides an epitope reversibly bound by a specific monoclonal antibody, enabling rapid assay and facile purification of expressed recombinant protein. A murine hybridoma designated 4E11 produces a monoclonal antibody that binds the FLAG® peptide in the presence of certain divalent metal cations, as described in U.S. Pat. No. 5,011,912, hereby incorporated by reference. The 4E11 hybridoma cell line has been deposited with the American Type Culture Collection under accession no. HB 9259. Monoclonal antibodies that bind the FLAG® peptide are available from Eastman Kodak Co., Scientific Imaging Systems Division, New Haven, Conn. The FLAG® polypeptide is also specifically cleaved by bovine mucosal enterokinase, allowing removal of the peptide from the purified protein; fusion proteins capped with such peptides may also be resistant to intracellular degradation in *E. coli*.

Additional, useful tag proteins include green fluorescent protein (GFP; Chalfie et al., *Science* 263:802, 1994), an N-terminal peptide that contains recognition sites for a monoclonal antibody, a specific endopeptidase, and a site-specific protein kinase (PKA; Blanar and Rutter, *Science* 256:1014, 1992), birA (Altman et al., *Science* 274:94, 1996) .and glutathione S transferase (GST: Smith and Johnson, *Gene* 67:31, 1988).

Fusion proteins further comprise the amino acid sequence of a DCTSP linked to an immunoglobulin Fc region. Fragments of an Fc region may also be used, as can Fc muteins. For example, certain residues within the hinge region of an Fc region are critical for high affinity binding to Fc receptors; mutations changing or eliminating such residues (alone or in combination) can be made in an Fc region to decrease the affinity of the Fc for Fc receptor. Depending on the portion of the Fc region used, a fusion protein may be expressed as a dimer, through formation of interchain disulfide bonds. If the fusion proteins are made with both heavy and light chains of an antibody, it is possible to form a protein oligomer with as many as four DCTSP regions.

In another embodiment, DCTSP proteins further comprise an oligomerizing peptide such as a zipper domain. Zipper domain is a term used to refer to a conserved peptide domain present in these (and other) proteins, which is responsible for oligomerization of the proteins. The zipper domain (also referred to herein as an oligomerizing, or oligomer-forming, domain) comprises a repetitive heptad repeat, with four or five leucine, isoleucine or valine residues interspersed with other amino acids. Numerous examples of zipper domains are known in the art, as are methods of making oligomeric proteins using them (see U.S. Pat. No. 5,716,805, issued Feb. 10, 1998).

Alternatively, the oligomer is a fusion polypeptide comprising multiple DCTSP polypeptides, with or without peptide linkers (spacer peptides). Among the suitable peptide linkers are those described in U.S. Pat. Nos. 4,751,180 and 4,935,233. Moreover, one can link two soluble DCTSP domains with a $Gly_4SerGly_5Ser$ linker sequence, or other linker sequence described in U.S. Pat. No. 5,073,627, which is incorporated by reference herein. A DNA sequence encoding a desired peptide linker can be inserted between, and in the same reading frame as, the DNA sequences of the invention, using any suitable conventional technique. For example, a chemically synthesized oligonucleotide encoding the linker can be ligated between the sequences. In particular embodiments, a fusion polypeptide comprises from two to four soluble DCTSP polypeptides, separated by peptide linkers. Suitable peptide linkers, their combination with other polypeptides, and their use are well known by those skilled in the art.

Also included within the scope of the invention are fragments or derivatives of the intracellular domain of DCTSP. Such fragments are prepared by any of the hereinmentioned techniques, and include peptides that are derived from the cytoplasmic domain of DCTSP as shown in SEQ ID NO:2 (amino acids 1 through 75), and those that comprise a portion of the cytoplasmic region. All techniques used in preparing soluble forms may also be used in preparing fragments or analogs of the cytoplasmic domain (i.e., RT-PCR techniques or use of selected restriction enzymes to prepare truncations). DNAs encoding all or a fragment of the cytoplasmic domain will be useful in identifying other proteins that are associated with DCTSP signaling, for example using immunoprecipitation techniques described herein, or another technique such as a yeast two-hybrid system.

The present invention also includes DCTSP with or without associated native-pattern glycosylation. Proteins expressed in yeast or mammalian expression systems, e.g., COS-7 cells, may be similar or slightly different in molecular weight and glycosylation pattern than the native molecules, depending upon the expression system. Expression of DNAs encoding the inventive proteins in bacteria such as *E. coli* provides non-glycosylated molecules. Glycosyl groups can be removed through conventional methods, in particular those utilizing glycopeptidase.

Functional mutant analogs of DCTSP protein having inactivated N-glycosylation sites can be produced by oligonucleotide synthesis and ligation or by site-specific mutagenesis techniques. These analog proteins can be produced in a homogeneous, reduced-carbohydrate form in good yield using yeast expression systems. N-glycosylation sites in eukaryotic proteins are characterized by the amino acid triplet Asn-$A_1$-Z, where $A_1$ is any amino acid except Pro, and Z is Ser or Thr. In this sequence, asparagine provides a side chain amino group for covalent attachment of carbohydrate. Such a site can be eliminated by substituting another amino acid for Asn or for residue Z, deleting Asn or Z, or inserting a non-Z amino acid between $A_1$ and Z, or an amino acid other than Asn between Asn and $A_1$. The canonical N-linked glycosylation sites in human DCTSP are shown in FIG. 1.

DCTSP protein derivatives may also be obtained by mutations of the native DCTSP or subunits thereof. A DCTSP mutated protein (mutein), as referred to herein, is a polypeptide homologous to a native DCTSP protein, but which has an amino acid sequence different from the native protein because of from one to ten amino acid deletions, insertions or substitutions. The effect of any mutation made in a DNA encoding a mutated peptide may be easily determined by analyzing the enzymatic activity of DCTSP. Moreover, activity of DCTSP analogs, muteins or derivatives can be determined by any of the assays described herein.

Analogs of the inventive proteins may be constructed by, for example, making various substitutions of residues or sequences or deleting terminal or internal residues or sequences not needed for biological activity. For example, cysteine residues can be deleted or replaced with other amino acids to prevent formation of incorrect intramolecular disulfide bridges upon renaturation. Other approaches to mutagenesis involve modification of adjacent dibasic amino acid residues to enhance expression in yeast systems in which KEX2 protease activity is present. Additionally, a single amino acid could be changed at one of the residues comprising the catalytic triad, thereby rendering the protease catalytically inactive. Over-expression of a catalytically inactive form of DCTSP could function as a dominant negative mutant.

When a deletion or insertion strategy is adopted, the potential effect of the deletion or insertion on biological activity should be considered. Subunits of the inventive proteins may be constructed by deleting terminal or internal residues or sequences. Soluble forms of DCTSP can be readily prepared and tested for serine protease activity. Polypeptides corresponding to the cytoplasmic regions, and fragments thereof can be prepared by similar techniques. Additional guidance as to the types of mutations that can be made is provided by a comparison of the sequence of DCTSP to proteins that have similar structures, as well as by performing structural analysis of the inventive DCTSP proteins.

In some instances, substitutions should preferentially be made conservatively; i.e., the most preferred substitute amino acids are those which do not affect the biological activity of DCTSP (i.e., ability of the inventive proteins to bind antibodies to the corresponding native protein in substantially equivalent a manner, the ability hydrolyze substrate, or the ability to transduce a DCTSP signal). Examples of conservative substitutions include substitution of amino acids outside of the binding domain(s) (either substrate or antibody binding areas for the extracellular domain, or regions that interact with other, intracellular proteins for the cytoplasmic domain), and substitution of amino acids that do not alter the secondary and/or tertiary structure of the native protein. Additional examples include substituting one aliphatic residue for another, such as Be, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known.

Mutations in nucleotide sequences constructed for expression of analog proteins or fragments thereof must, of course, preserve the reading frame phase of the coding sequences and preferably will not create complementary regions that could hybridize to produce secondary mRNA structures such as loops or hairpins which would adversely affect translation of the mRNA.

Not all mutations in the nucleotide sequence which encodes a DCTSP protein or fragments thereof will be expressed in the final product, for example, nucleotide substitutions may be made to enhance expression, primarily to avoid secondary structure loops in the transcribed mRNA (see EPA 75,444A, incorporated herein by reference), or to provide codons that are more readily translated by the selected host, e.g., the well-known *E. coli* preference codons for *E. coli* expression.

Although a mutation site may be predetermined, it is not necessary that the nature of the mutation per se be predetermined. For example, in order to select for optimum characteristics of mutants, random mutagenesis may be conducted and the expressed mutated proteins screened for the desired activity. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques, Jan.* 12–19, 1985,); Smith et al. (*Genetic Engineering: Principles and Methods*, Plenum Press, 1981); and U.S. Pat. Nos. 4,518,584 and 4,737,462 disclose suitable techniques, and are incorporated by reference herein.

Other embodiments of the inventive proteins include DCTSP polypeptides encoded by DNAs capable of hybridizing to the DNA of SEQ ID NO:1 under moderately stringent conditions (prewashing solution of 5×SSC, 0.5% SDS, 1.0 mM EDTA (pH 8.0) and hybridization conditions of 50 degrees C., 5×SSC, overnight) to the DNA sequences encoding DCTSP, or more preferably under stringent conditions (for example, hybridization in 6×SSC at 63 degrees C. overnight; washing in 3×SSC at 55 degrees C.), and other sequences which are degenerate to those which encode the DCTSP. In one embodiment, DCTSP polypeptides are at least about 70% identical in amino acid sequence to the amino acid sequence of native DCTSP protein as set forth in SEQ ID NO:2. In a preferred embodiment, DCTSP polypeptides are at least about 80% identical in amino acid sequence to the native form of DCTSP; more preferred polypeptides are those that are at least about 90% identical to native DCTSP; most preferred polypeptides are those that are at least about 95% identical to native DCTSP.

Percent identity may be determined by visual inspection and mathematical calculation, or by using a computer program. Preferably, the comparison is done using a computer program. An exemplary, preferred computer program is the Genetics Computer Group (GCG; Madison, Wis.) Wisconsin package version 10.0 program, 'GAP.' The preferred default parameters for the 'GAP' program includes: (1) The GCG implementation of the previously stated comparison matrixes for nucleotides and amino acids; (2) a penalty of 30 for each gap and an additional penalty of 1 for each symbol in each gap for amino acid sequences, or penalty of 50 for each gap and an additional penalty of 3 for each symbol in each gap for nucleotide sequences; (3) no penalty for end gaps; and (4) no maximum penalty for long gaps. Other programs used by one skilled in the art of sequence comparison may also be used. For fragments derived from the DCTSP protein, the identity is calculated based on that portion of the DCTSP protein that is present in the fragment The biological activity of DCTSP analogs or muteins can be determined by testing the ability of the analogs or muteins to hydrolyze substrate, or to share another activity (i.e., substrate binding, or binding to an antibody that binds native DCTSP) with a native DCTSP. Suitable assays, for example, an enzyme immunoassay or a dot blot, employing an antibody that binds native DCTSP, can be used to assess the activity of DCTSP analogs or muteins, as can assays of protease activity. Suitable assays also include, for example, signal transduction assays and methods that evaluate the ability of the cytoplasmic region of DCTSP to associate with other intracellular proteins involved in signal transduction or cytoskeletal organization. Such methods are well known in the art.

DNAs encoding any or all of the aforementioned DCTSP polypeptides are also encompassed in the present invention. Furthermore, fragments of the DCTSP nucleotide sequences are also useful. In one embodiment, such fragments comprise at least 17 consecutive nucleotides, preferably at least 25 nucleotides, more preferably at least 30 consecutive nucleotides, of the DCTSP DNA disclosed herein. In another embodiment, such fragments comprise at least 300 consecutive nucleotides, preferably at least 400 nucleotides, more preferably at least 500 consecutive nucleotides, of the DCTSP DNA disclosed herein. DNA and RNA complements of such fragments are provided herein, along with both single-stranded and double-stranded forms of the DCTSP DNA of SEQ ID NOs:1, or 3, and those encoding the aforementioned polypeptides. Such nucleic acid fragments (for example, a probe corresponding to the extracellular domain of DCTSP) are used as a probe or as primers in a polymerase chain reaction (PCR).

The probes also find use in detecting the presence of DCTSP nucleic acids in in vitro assays and in such procedures as Northern and Southern blots. Cell types expressing DCTSP can be identified as well. Such procedures are well known, and the skilled artisan can choose a probe of suitable length, depending on the particular intended application. For PCR, 5' and 3' primers corresponding to the termini of a desired DCTSP DNA sequence are employed to amplify that sequence, using conventional techniques.

Other useful fragments of the DCTSP nucleic acids are antisense or sense oligonucleotides comprising a single-stranded nucleic acid sequence (either RNA or DNA) capable of binding to target DCTSP mRNA (sense) or DCTSP DNA (antisense) sequences. The ability to create an antisense or a sense oligonucleotide, based upon a cDNA sequence for a given protein is described in, for example, Stein and Cohen, *Cancer Res.* 48:2659, 1988 and van der Krol et al., *BioTechniques* 6:958, 1988.

In certain other embodiments of the invention, antagonists can be designed to reduce the level of endogenous DCTSP gene expression, e.g., using well-known antisense or ribozyme approaches to inhibit or prevent translation of DCTSP mRNA transcripts; triple helix approaches to inhibit transcription of DCTSP family genes; or targeted homologous recombination to inactivate or "knock out" the DCTSP genes or their endogenous promoters or enhancer elements. Such antisense, ribozyme, and triple helix antagonists can be designed to reduce or inhibit either unimpaired, or if appropriate, mutant DCTSP gene activity. Techniques for the production and use of such molecules are well known to those of skill in the art.

Antisense RNA and DNA molecules act to directly block the translation of mRNA by hybridizing to targeted mRNA and preventing polypeptide translation. Antisense approaches involve the design of oligonucleotides (either DNA or RNA) that are complementary to a DCTSP mRNA. The antisense oligonucleotides will bind to the complementary target gene mRNA transcripts and prevent translation. Absolute complementarity, although preferred, is not required. A sequence "complementary" to a portion of a nucleic acid, as referred to herein, means a sequence having sufficient complementarity to be able to hybridize with the nucleic acid, forming a stable duplex (or triplex, as appropriate). In the case of double-stranded antisense nucleic acids, a single strand of the duplex DNA can thus be tested, or triplex formation can be assayed. The ability to hybridize will depend on both the degree of complementarity and the length of the antisense nucleic acid. Preferred oligonucleotides are complementary to the 5' end of the message, e.g., the 5' untranslated sequence up to and including the AUG initiation codon. However, oligonucleotides complementary to the 5'- or 3'-non-translated, non-coding regions of the DCTSP gene transcript, or to the coding regions, could be used in an antisense approach to inhibit translation of endogenous DCTSP mRNA. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The oligonucleotides can be DNA or RNA or chimeric mixtures or derivatives or modified versions thereof, single-stranded or double-stranded. Chimeric oligonucleotides, oligonucleosides, or mixed oligonucleotides/oligonucleosides of the invention can be of several different types. These include a first type wherein the "gap" segment of nucleotides is positioned between 5' and 3' "wing" segments of linked nucleosides and a second "open end" type wherein the "gap" segment is located at either the 3' or the 5' terminus of the oligomeric compound (see, e.g., U.S. Pat. No. 5,985,664). Oligonucleotides of the first type are also known in the art as "gapmers" or gapped oligonucleotides. Oligonucleotides of the second type are also known in the art as "hemimers" or "wingmers".

The oligonucleotide can be modified at the base moiety, sugar moiety, or phosphate backbone, for example, to improve stability of the molecule, hybridization, etc. The oligonucleotide can include other appended groups such as peptides (e.g., for targeting host cell receptors in vivo), or agents facilitating transport across the cell membrane (see, e.g., Letsinger et al., 1989, *Proc Natl Acad Sci USA* 86:6553; Lemaitre et al., 1987, *Proc Natl Acad Sci USA* 84:648; PCT Publication No. WO88/09810), or hybridization-triggered cleavage agents or intercalating agents. (See, e.g., Zon, 1988, *Pharm. Res.* 5:539).

The antisense molecules should be delivered to cells which express the DCTSP transcript in vivo. A number of methods have been developed for delivering antisense DNA or RNA to cells; e.g., antisense molecules can be injected directly into the tissue or cell derivation site, or modified antisense molecules, designed to target the desired cells (e.g., antisense linked to peptides or antibodies that specifically bind receptors or antigens expressed on the target cell surface) can be administered systemically. However, it is often difficult to achieve intracellular concentrations of the antisense sufficient to suppress translation of endogenous mRNAs.

A preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous DCTSP gene transcripts and thereby prevent translation of the DCTSP mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells.

Ribozyme molecules designed to catalytically cleave DCTSP mRNA transcripts can also be used to prevent translation of DCTSP mRNA and expression of DCTSP polypeptides. (See, e.g., PCT International Publication WO90/11364 and U.S. Pat. No. 5,824,519). The ribozymes that can be used in the present invention include hammerhead ribozymes (Haseloff and Gerlach, 1988, *Nature*, 334:585), RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (International Patent Application No. WO 88/04300; Been and Cech, 1986, Cell, 47:207). As in the antisense approach, the ribozymes can be composed of modified oligonucleotides (e.g. for improved stability, targeting, etc.) and should be delivered to cells which express the DCTSP polypeptide in vivo. A preferred method of delivery involves using a DNA construct "encoding" the ribozyme under the control of a strong constitutive pol III or pol II promoter, so that transfected cells will produce sufficient quantities of the ribozyme to destroy endogenous DCTSP messages and inhibit translation. Because ribozymes, unlike antisense molecules, are catalytic, a lower intracellular concentration is required for efficiency.

Alternatively, endogenous DCTSP gene expression can be reduced by targeting deoxyribonucleotide sequences complementary to the regulatory region of the target gene (i.e., the target gene promoter and/or enhancers) to form triple helical structures that prevent transcription of the target DCTSP gene. (See generally, Helene, 1991, *Anticancer Drug Des.*, 6:569; Helene, et al., 1992, *Ann. N.Y. Acad. Sci.*, 660:27; and Maher, 1992, *Bioassays* 14:807).

Anti-sense RNA and DNA, ribozyme, and triple helix molecules of the invention can be prepared by any method known in the art for the synthesis of DNA and RNA molecules. These include techniques for chemically synthesizing oligodeoxy-ribonucleotides and oligoribonucleotides well known in the art such as for example solid phase phosphoramidite chemical synthesis. Oligonucleotides can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al., 1988, *Nucl. Acids Res.* 16:3209. Methylphosphonate oligonucleotides can be prepared by use of controlled pore glass polymer supports (Sarin et al., 1988, *Proc. Natl. Acad. Sci. USA* 85:7448).

Alternatively, RNA molecules can be generated by in vitro and in vivo transcription of DNA sequences encoding the antisense RNA molecule. Such DNA sequences can be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Endogenous target gene expression can also be reduced by inactivating or "knocking out" the target gene or its promoter using targeted homologous recombination (e.g., Smithies, et al., 1985, *Nature* 317:230; Thomas and Capecchi, 1987, *Cell* 51:503; Thompson, et al., 1989, *Cell* 5:313). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene.

Such approaches are particularly suited to making modifications to ES (embryonic stem) cells that can be used to generate animal offspring with an inactive target gene (e.g., see Thomas and Capecchi, 1987 and Thompson, 1989, supra), or in model organisms such as *Caenorhabditis elegans* where the "RNA interference" ("RNAi") technique (Grishok, Tabara, and Mello, 2000, *Science* 287:2494), or the introduction of transgenes (Demburg et al., 2000, *Genes Dev.* 14:1578) are used to inhibit the expression of specific target genes. This approach can be adapted for use in humans provided the recombinant DNA constructs are directly administered or targeted to the required site in vivo using appropriate vectors such as viral vectors.

Uses of DNAs, Proteins and Analogs

The DCTSP DNAs, proteins and analogs described herein will have numerous uses, including the preparation of pharmaceutical compositions. For example, soluble forms of DCTSP will be useful for proteolytic hydrolysis of substrate. Soluble forms of DCTSP can also be used to detect or enumerate cells that bind DCTSP, and to deliver selected agents to such cells. Similarly, soluble DCTSP can be used on tissue samples, to type or enumerate cells therein. DCTSP compositions (both protein and DNAs) will also be useful in development of both agonistic and antagonistic antibodies to DCTSP.

The inventive proteins will also be useful in preparing kits that are used to detect soluble DCTSP, or monitor DCTSP-related activity, for example, in patient specimens. DCTSP proteins will also find uses in monitoring DCTSP-related activity in other samples or compositions, as is necessary when screening for antagonists, agonists or mimetics of this activity (for example, peptides or small molecules that inhibit, enhance or mimic, respectively, DCTSP activity). A variety of assay formats are useful in such kits, including (but not limited to) ELISA, dot blot, solid phase binding assays (such as those using a biosensor), rapid format assays and bioassays.

The purified DCTSP according to the invention will facilitate the discovery of agonists and/or antagonists of DCTSP, and thus, agents that are capable of modulating DCTSP serine protease activity. The use of a purified DCTSP polypeptide in the screening for potential agonists and/or antagonists is important and can virtually eliminate the possibility of interfering reactions with contaminants. Such a screening assay can utilize either the extracellular domain of DCTSP, the intracellular domain, or a fragment of either of these polypeptides. Detecting the inhibitory or agonistic activity of a molecule would typically involve use of a soluble form of DCTSP derived from the extracellular domain in a screening assay to detect molecules that bind to (and may be hydrolyzed by) DCTSP, or using a polypeptide derived from the intracellular domain in an assay to detect inhibition or enhancement of the interaction of DCTSP and other, intracellular proteins.

Moreover, in vitro systems can be used to ascertain the ability of molecules to antagonize or agonize DCTSP activity. Included in such methods are uses of DCTSP chimeras, for example, a chimera of the DCTSP intracellular domain and an extracellular domain derived from a protein having a known ligand. The effects on signal transduction or cytoskeletal organization of various molecules can then be monitored by utilizing the known ligand to transduce a signal.

In addition, DCTSP polypeptides can also be used for structure-based design of DCTSP agonists and/or antagonists. Such structure-based design is also known as "rational drug design." The DCTSP polypeptides can be three-dimensionally analyzed by, for example, X-ray crystallography, nuclear magnetic resonance or homology modeling, all of which are well-known methods. The use of DCTSP structural information in molecular modeling software systems to assist in inhibitor design is also encompassed by the invention. Such computer-assisted modeling and drug design may utilize information such as chemical conformational analysis, electrostatic potential of the molecules, protein folding, etc. A particular method of the invention comprises analyzing the three dimensional structure of DCTSP for likely binding sites of substrates, synthesizing a new molecule that incorporates a predictive reactive site, and assaying the new molecule as described above.

The inventive DNAs are useful for the expression of recombinant proteins, and as probes for analysis (either quantitative or qualitative) of the presence or distribution of DCTSP transcripts. The inventive DNAs are also useful in gene therapy techniques, for replacement of defective DCTSP DNA, or in treatment of infectious or neoplastic disease conditions in which it is useful to have cells expressing additional DCTSP. For such uses, either the full-length or the alternatively spliced versions disclosed herein can be utilized. Additional amino acids can be added between the transmembrane region and the extracellular domain to facilitate folding and/or activity of the resulting membrane-associated receptor. The inventive DNAs will also have use as probes or primers, and in the identification of human chromosome 11, or example in karyotypic or genetic analysis.

Expression of Recombinant DCTSP

The proteins of the present invention are preferably produced by recombinant DNA methods by inserting a DNA sequence encoding DCTSP protein or an analog thereof into a recombinant expression vector and expressing the DNA sequence in a recombinant expression system under conditions promoting expression. DNA sequences encoding the proteins provided by this invention can be assembled from cDNA fragments and short oligonucleotide linkers, or from a series of oligonucleotides, to provide a synthetic gene which is capable of being inserted in a recombinant expression vector and expressed in a recombinant transcriptional unit.

Recombinant expression vectors include synthetic or cDNA-derived DNA fragments encoding DCTSP, or homologs, muteins or bioequivalent analogs thereof, operably linked to suitable transcriptional or translational regulatory elements derived from mammalian, microbial, viral or insect genes. Such regulatory elements include a transcriptional promoter, an optional operator sequence to control transcription, a sequence encoding suitable mRNA ribosomal binding sites, and sequences which control the termination of transcription and translation, as described in detail below. The ability to replicate in a host, usually conferred by an origin of replication, and a selection gene to facilitate recognition of transformants may additionally be incorporated.

DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame. DNA sequences encoding DCTSP, or homologs or analogs thereof which are to be expressed in a microorganism will preferably contain no introns that could prematurely terminate transcription of DNA into mRNA.

Useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed. E. coli is typically transformed using derivatives of pBR322, a plasmid derived from an E. coli species (Bolivar et al., Gene 2:95, 1977). pBR322 contains genes for ampicillin and tetracycline resistance and thus provides simple means for identifying transformed cells.

Promoters commonly used in recombinant microbial expression vectors include the β-lactamase (penicillinase) and lactose promoter system (Chang et al., Nature 275:615, 1978; and Goeddel et al., Nature 281:544, 1979), the tryptophan (trp) promoter system (Goeddel et al., Nucl. Acids Res. 8:4057, 1980; and EPA 36,776) and tac promoter (Maniatis, Molecular Cloning: A Laboratory Manual, Cold Spring Harbor Laboratory, p. 412, 1982). A particularly useful bacterial expression system employs the phage λ $P_L$ promoter and cI857ts thermolabile repressor. Plasmid vectors available from the American Type Culture Collection which incorporate derivatives of the λ $P_L$ promoter include plasmid pHUB2, resident in E. coli strain JMB9 (ATCC 37092) and pPLc28, resident in E. coli RR1 (ATCC 53082).

Suitable promoter sequences in yeast vectors include the promoters for metallothionein, 3-phosphoglycerate kinase (Hitzeman et al., J. Biol. Chem. 255:2073, 1980) or other glycolytic enzymes (Hess et al., J. Adv. Enzyme Reg. 7:149, 1968; and Holland et al., Biochem. 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPA 73,657.

Preferred yeast vectors can be assembled using DNA sequences from pBR322 for selection and replication in *E. coli* (Amp$^r$ gene and origin of replication) and yeast DNA sequences including a glucose-repressible ADH2 promoter and α-factor secretion leader. The ADH2 promoter has been described by Russell et al. (*J. Biol. Chem.* 258:2674, 1982) and Beier et al. (*Nature* 300:724, 1982). The yeast α-factor leader, which directs secretion of heterologous proteins, can be inserted between the promoter and the structural gene to be expressed. See, e.g., Kurjan et al., *Cell* 30:933, 1982; and Bitter et al., *Proc. Natl. Acad. Sci. USA* 81:5330, 1984. The leader sequence may be modified to contain, near its 3' end, one or more useful restriction sites to facilitate fusion of the leader sequence to foreign genes.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., *Nature* 273:113, 1978). Smaller or larger SV40 fragments may also be used, provided the approximately 250 bp sequence extending from the Hind III site toward the BglI site located in the viral origin of replication is included. Further, viral genomic promoter, control and/or signal sequences may be utilized, provided such control sequences are compatible with the host cell chosen. Exemplary vectors can be constructed as disclosed by Okayama and Berg (*Mol. Cell. Biol.* 3:280, 1983).

A useful system for stable high level expression of mammalian receptor cDNAs in C127 murine mammary epithelial cells can be constructed substantially as described by Cosman et al. (*Mol. Immunol.* 23:935, 1986). A preferred eukaryotic vector for expression of DCTSP DNA is referred to as pDC406 (McMahan et al., *EMBO J.* 10:2821, 1991), and includes regulatory sequences derived from SV40, human immunodeficiency virus (HIV), and Epstein-Barr virus (EBV). Other preferred vectors include pDC409 and pDC410, which are derived from pDC406. pDC410 was derived from pDC406 by substituting the EBV origin of replication with sequences encoding the SV40 large T antigen. pDC409 differs from pDC406 in that a Bgl II restriction site outside of the multiple cloning site has been deleted, making the Bgl II site within the multiple cloning site unique.

A useful cell line that allows for episomal replication of expression vectors, such as pDC406 and pDC409, which contain the EBV origin of replication, is CV-1/EBNA (ATCC CRL 10478). The CV-1/EBNA cell line was derived by transfection of the CV-1 cell line with a gene encoding Epstein-Barr virus nuclear antigen-1 (EBNA-1) and constitutively express EBNA-1 driven from human CMV immediate-early enhancer/promoter.

Host Cells

Transformed host cells are cells which have been transformed or transfected with expression vectors constructed using recombinant DNA techniques and which contain sequences encoding the proteins of the present invention. Transformed host cells may express the desired protein (DCTSP, or homologs or analogs thereof), but host cells transformed for purposes of cloning or amplifying the inventive DNA do not need to express the protein. Expressed proteins will preferably be secreted into the culture supernatant, depending on the DNA selected, but may be deposited in the cell membrane.

Suitable host cells for expression of proteins include prokaryotes, yeast or higher eukaryotic cells under the control of appropriate promoters. Prokaryotes include gram negative or gram positive organisms, for example *E. coli* or *Bacillus* spp. Higher eukaryotic cells include established cell lines of mammalian origin as described below. Cell-free translation systems could also be employed to produce proteins using RNAs derived from the DNA constructs disclosed herein. Appropriate cloning and expression vectors for use with bacterial, fungal, yeast, and mammalian cellular hosts are described by Pouwels et al. (*Cloning Vectors: A Laboratory Manual*, Elsevier, N.Y., 1985), the relevant disclosure of which is hereby incorporated by reference.

Prokaryotic expression hosts may be used for expression of DCTSP, or homologs or analogs thereof that do not require extensive proteolytic and disulfide processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include *E. coli, Bacillus subtilis, Salmonella typhimurium*, and various species within the genera Pseudomonas, Streptomyces, and Staphylococcus, although others may also be employed as a matter of choice.

Recombinant DCTSP may also be expressed in yeast hosts, preferably from the Saccharomyces species, such as *S. cerevisiae*. Yeast of other genera, such as Pichia or Kluyveromyces may also be employed. Yeast vectors will generally contain an origin of replication from the 2 μ yeast plasmid or an autonomously replicating sequence (ARS), promoter, DNA encoding the protein, sequences for polyadenylation and transcription termination and a selection gene. Preferably, yeast vectors will include an origin of replication and selectable marker permitting transformation of both yeast and *E. coli*, e.g., the ampicillin resistance gene of *E. coli* and *S. cerevisiae* trp1 gene, which provides a selection marker for a mutant strain of yeast lacking the ability to grow in tryptophan, and a promoter derived from a highly expressed yeast gene to induce transcription of a structural sequence downstream. The presence of the trp 1 lesion in the yeast host cell genome then provides an effective environment for detecting transformation by growth in the absence of tryptophan.

Suitable yeast transformation protocols are known to those of skill in the art; an exemplary technique is described by Hinnen et al., *Proc. Natl. Acad. Sci. USA* 75:1929, 1978, selecting for Trp$^+$ transformants in a selective medium consisting of 0.67% yeast nitrogen base, 0.5% casamino acids, 2% glucose, 10 μg/ml adenine and 20 μg/ml uracil. Host strains transformed by vectors comprising the ADH2 promoter may be grown for expression in a rich medium consisting of 1% yeast extract, 2% peptone, and 1% glucose supplemented with 80 μg/ml adenine and 80 μg/ml uracil. Derepression of the ADH2 promoter occurs upon exhaustion of medium glucose. Crude yeast supernatants are harvested by filtration and held at 4° C. prior to further purification.

Various mammalian or insect cell culture systems can be employed to express recombinant protein. Baculovirus systems for production of heterologous proteins in insect cells are reviewed by Luckow and Summers, *Bio/Technology* 6:47 (1988). Examples of suitable mammalian host cell lines include the COS-7 lines of monkey kidney cells, described by Gluzman (*Cell* 23:175, 1981), and other cell lines capable of expressing an appropriate vector including, for example, CV-1/EBNA (ATCC CRL 10478), L cells, C127, 3T3, Chinese hamster ovary (CHO), HeLa and BHK cell lines. Mammalian expression vectors may comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences.

Purification of Recombinant DCTSP

Purified DCTSP, and homologs or analogs thereof are prepared by culturing suitable host/vector systems to express the recombinant translation products of the DNAs of the present invention, which are then purified from culture media or cell extracts. For example, supernatants from systems which secrete recombinant protein into culture media can be first concentrated using a commercially available protein concentration filter, for example, an Amicon or Millipore Pellicon ultrafiltration unit.

Following the concentration step, the concentrate can be applied to a suitable purification matrix. For example, a suitable affinity matrix can comprise a counter structure protein or lectin or antibody molecule bound to a suitable support. Alternatively, an anion exchange resin can be employed, for example, a matrix or resin having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Gel filtration chromatography also provides a means of purifying the inventive proteins.

Affinity chromatography is a particularly preferred method of purifying DCTSP and homologs thereof. For example, a DCTSP expressed as a fusion protein comprising an immunoglobulin Fc region can be purified using Protein A or Protein G affinity chromatography. Moreover, a DCTSP protein comprising an oligomerizing zipper domain may be purified on a resin comprising an antibody specific to the oligomerizing zipper domain. Monoclonal antibodies against the DCTSP protein may also be useful in affinity chromatography purification, by utilizing methods that are well-known in the art. A ligand may also be used to prepare an affinity matrix for affinity purification of DCTSP. Those of skill in the art are aware of other affinity purification methods that are useful for purifying DCTSP proteins expressed as fusion proteins with a selected tag (for example, poly-His-tagged DCTSP purified using nickel-NTA resin, or FLAG®-tagged DCTSP using anti-FLAG® affinity resin).

Finally, one or more reversed-phase high performance liquid chromatography (RP-HPLC) steps employing hydrophobic RP-HPLC media, e.g., silica gel having pendant methyl or other aliphatic groups, can be employed to further purify a DCTSP composition. Some or all of the foregoing purification steps, in various combinations, can also be employed to provide a homogeneous recombinant protein.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant protein can be disrupted by any convenient method, including freeze-thaw cycling, sonication, mechanical disruption, or use of cell lysing agents.

Fermentation of yeast which express the inventive protein as a secreted protein greatly simplifies purification. Secreted recombinant protein resulting from a large-scale fermentation can be purified by methods analogous to those disclosed by Urdal et al. (*J. Chromatog.* 296:171, 1984). This reference describes two sequential, reversed-phase HPLC steps for purification of recombinant human GM-CSF on a preparative HPLC column.

Protein synthesized in recombinant culture is characterized by the presence of cell components, including proteins, in amounts and of a character which depend upon the purification steps taken to recover the inventive protein from the culture. These components ordinarily will be of yeast, prokaryotic or non-human higher eukaryotic origin and preferably are present in innocuous contaminant quantities, on the order of less than about 1 percent by weight. Further, recombinant cell culture enables the production of the inventive proteins free of other proteins which may be normally associated with the proteins as they are found in nature in the species of origin.

Uses and Administration of DCTSP Compositions

The present invention provides methods of using therapeutic compositions comprising an effective amount of a protein and a suitable diluent and carrier, and methods for regulating an immune or inflammatory response. The use of DCTSP in conjunction with soluble cytokine receptors or cytokines, or other immunoregulatory molecules is also contemplated.

For therapeutic use, purified protein is administered to a patient, preferably a human, for treatment in a manner appropriate to the indication. Thus, for example, DCTSP protein compositions administered to regulate immune function can be given by bolus injection, continuous infusion, sustained release from implants, or other suitable technique. Typically, a therapeutic agent will be administered in the form of a composition comprising purified DCTSP, in conjunction with physiologically acceptable carriers, excipients or diluents. Such carriers will be relatively nontoxic to recipients at the dosages and concentrations employed.

Ordinarily, the preparation of such protein compositions entails combining the inventive protein with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with conspecific serum albumin are exemplary appropriate diluents. Preferably, product is formulated as a lyophilizate using appropriate excipient solutions (e.g., sucrose) as diluents. Appropriate dosages can be determined in trials. The amount and frequency of administration will depend, of course, on such factors as the nature and severity of the indication being treated, the desired response, the condition of the patient, and so forth.

Screening Assays Using DCTSP Compositions

Specific screening methods are known in the art and along with integrated robotic systems and collections of chemical compounds/natural products are extensively incorporated in high throughput screening so that large numbers of test compounds can be tested for antagonist or agonist activity within a short amount of time. These methods include homogeneous assay formats such as fluorescence resonance energy transfer, fluorescence polarization, time-resolved fluorescence resonance energy transfer, scintillation proximity assays, reporter gene assays, fluorescence quenched enzyme substrate, chromogenic enzyme substrate and electrochemiluminescence, as well as more traditional heterogeneous assay formats such as enzyme-linked immunosorbant assays (ELISA) or radioimmunoassays. Also comprehended herein are cell-based assays, for example those utilizing reporter genes, as well as functional assays that analyze the effect of an antagonist or agonist on biological function(s).

Moreover, combinations of screening assays can be used to find molecules that regulate the biological activity of DCTSP. Molecules that regulate the biological activity of a polypeptide may be useful as agonists or antagonists of the peptide. In using combinations of various assays, it is usually first determined whether a candidate molecule binds to a polypeptide by using an assay that is amenable to high throughput screening. Binding candidate molecules identified in this manner are then added to a biological assay to determine biological effects. Molecules that bind and that have an agonistic or antagonistic effect on biologic activity will be useful in treating or preventing disease or conditions with which the polypeptide(s) are implicated. The assays disclosed herein may also be used to evaluate the ability of variants of DCTSP (for example, a splice variant disclosed herein or other variant lacking all or a portion of the stem region) to bind particular molecules. Differential binding ability between various forms of DCTSP can be exploited to selectively modulate particular activities. Moreover, variants of DCTSP that lack an enzymatically-active catalytic domain can also be used as disclosed herein, to evaluate that ability of substrate(s) to bind DCTSP, and identify molecules capable of modulating such binding.

Homogeneous assays are mix-and-read style assays that are very amenable to robotic application, whereas heterogeneous assays require separation of free from bound analyte by more complex unit operations such as filtration, centrifugation or washing. These assays are utilized to detect a wide variety of specific biomolecular interactions (including protein-protein, receptor-ligand, enzyme-substrate, and so on), and the inhibition thereof by small organic molecules. These assay methods and techniques are well known in the art (see, e.g., High Throughput Screening: The Discovery of Bioactive Substances, John P. Devlin (ed.), Marcel Dekker, New York, 1997 ISBN: 0-8247-0067-8). The screening assays of the present invention are amenable to high throughput screening of chemical libraries and are suitable for the identification of small molecule drug candidates, antibodies, peptides, and other antagonists and/or agonists, natural or synthetic.

One such assay is based on fluorescence resonance energy transfer (FRET; for example, HTRF®, Packard Instrument Company, Meriden, Cont.; LANCE™, PerkinElmer LifeSciences, Wallac Oy., Turku, Finland) between two fluorescent labels, an energy donating long-lived chelate label and a short-lived organic acceptor. The energy transfer occurs when the two labels are brought in close proximity via the molecular interaction between DCTSP and substrate. In a FRET assay for detecting inhibition of the binding of DCTSP and substrate, europium chelate or cryptate labeled DCTSP or substrate serves as an energy donor and streptavidin-labeled allophycocyanin (APC) bound to the appropriate binding partner (i.e., DCTSP if substrate is labeled, or substrate if DCTSP is labeled) serves as an energy acceptor. Once DCTSP binds substrate, the donor and acceptor molecules are brought in close proximity, and energy transfer occurs, generating a fluorescent signal at 665 nm. Antagonists of the interaction of DCTSP and substrate will thus inhibit the fluorescent signal, whereas agonists of this interaction would enhance it.

DELFIA® (dissociated enhanced lanthanide fluoroimmunoassay; PerkinElmer LifeSciences, Wallac Oy., Turku, Finland) is a solid-phase assay based on time-resolved fluorometry analysis of lanthanide chelates (see, for example, U.S. Pat. No. 4,565,790, issued Jan. 21, 1986). For this type of assay, microwell plates are coated with a first protein (DCTSP or substrate). The binding partner (substrate or DCTSP, respectively) is conjugated to europium chelate or cryptate, and added to the plates. After suitable incubation, the plates are washed and a solution that dissociates europium ions from solid phase bound protein, into solution, to form highly fluorescent chelates with ligands present in the solution, after which the plates are read using a plate reader such as a VICTOR$^{2}$™ (PerkinElmer LifeSciences, Wallac Oy., Turku, Finland) plate reader to detect emission at 615 nm.

Another assay that will be useful in the inventive methods is a FlashPlate® (Packard Instrument Company, IL)-based assay. This assay measures the ability of compounds to inhibit protein-protein interactions. FlashPlates® are coated with a first protein (either DCTSP or substrate), then washed to remove excess protein. For the assay, compounds to be tested are incubated with the second protein (substrate, if the plates are coated with DCTSP, or DCTSP if plates are coated with substrate) and $I^{125}$ labeled antibody against the second protein and added to the plates. After suitable incubation and washing, the amount of radioactivity bound is measured using a scintillation counter (such as a MicroBeta® counter; PerkinElmer LifeSciences, Wallac Oy., Turku, Finland).

The AlphaScreen™ assay (Packard Instrument Company, Meriden, Cont.). AlphaScreen™ technology is an "Amplified Luminescent Proximity Homogeneous Assay" method utilizing latex microbeads (250 nm diameter) containing a photosensitizer (donor beads), or chemiluminescent groups and fluorescent acceptor molecules (acceptor beads). Upon illumination with laser light at 680 nm, the photosensitizer in the donor bead converts ambient oxygen to singlet-state oxygen. The excited singlet-state oxygen molecules diffuse approximately 250 nm (one bead diameter) before rapidly decaying. If the acceptor bead is in close proximity to the donor bead (i.e., by virtue of the interaction of DCTSP and substrate), the singlet-state oxygen molecules reacts with chemiluminescent groups in the acceptor beads, which immediately transfer energy to fluorescent acceptors in the same bead. These fluorescent acceptors shift the emission wavelength to 520–620 nm, resulting in a detectable signal. Antagonists of the interaction of DCTSP with substrate will thus inhibit the shift in emission wavelength, whereas agonists of this interaction would enhance it.

One embodiment of a method for identifying molecules which inhibit or antagonize DCTSP-mediated signaling involves adding a candidate molecule to a medium which contains cells that express DCTSP; changing the conditions of said medium so that, but for the presence of the candidate molecule, DCTSP would be bound to substrate, and observing the binding and stimulation or inhibition of a functional response. The activity of the cells that were contacted with the candidate molecule may then be compared with the identical cells that were not contacted and antagonists and agonists of the polypeptides of the instant invention may be identified. The measurement of biological activity may be performed by a number of well-known methods such as measuring the amount of protein present (e.g. an ELISA) or of the protein's activity. A decrease in biological stimulation or activation would indicate an antagonist. An increase would indicate an agonist.

Other useful assays include protease assays that are known in the art such as those described in the *Handbook of Proteolytic Enzymes*, Barrett et al., eds. supra. Typical spectroscopic assays for trypsin-like serine proteases could use any number of commercially available substrates, such as, but not limited by: Bz-Arg-OEt (BAEE), Tos-Arg-OMe (TAME), Z-Gly-Pro-Arg-NHMec or Suc-Ala-Ala-Pro-Arg-NHPhNO2. One of ordinary skill in the art would recognize that such an assay would be performed in an appropriate buffer, e.g Tris-HCL, Hepes, or phosphate at pH in the range of pH 7–8, and would likely contain moderate amounts of $CaCl_2$ (10 mM) which is known to stabilize some proteases and therefore maximize their activity. Assays are conventionally performed at 37 degrees C. for times ranging from a few seconds to many minutes or longer depending on the purpose of the assay. Evidence of proteolysis is detected spectrophotometrically at the proper wavelength; the wavelength being dictated by the absorption properties of the leaving group cleaved off the substrate.

Computer Analysis of Assay Results

In one aspect of the invention, the assays of the invention are used to identify compounds that alter DCTSP signaling activity. The benefits of integrated robotic systems used to analyze collections of chemical compounds/natural products in such assays, which preferably incorporate high-throughput screening methods, are most often realized by the use of sophisticated computer and statistical techniques to manage the resulting data. In one form, the information generated in the inventive screening assays is stored (or compiled) in electronic form, using a computerized database that allows information to be efficiently catalogued and retrieved. Such databases are comprised of records, usually one record for each compound, that includes information about the compound, such as chemical name, structure, source, activity in a binding assay, activity in a biological assay, etc.

The information may be entered into the database manually, that is by a user entering data through a user interface (i.e., keyboard, touchpad, etc.), or it may be entered electronically as in when a robotic system for analysis of compounds generates electronic results that are transferred to another computer system (often referred to as uploading). Such information is usually stored in a discrete area of the record referred to as a field. Additionally, the information, preferably in the form of a database, may be stored permanently or temporarily on various forms of storage media, including paper, the brains of living organisms, compact disks, floppy disks, magnetic tapes, optical tapes, hard drives, computer system memory units, and the like.

The database may be stand-alone, or the records therein may be related to other databases (a relational database). Examples of other databases include publicly available, well-known databases such as GenBank for peptides and nucleic acids (and associated databases maintained by the National Center for Biotechnology Information or NCBI), and the databases available through www.chemfinder.com or The Dialog Corporation (Cary, N.C.) for chemical compounds.

A user will be able to search the database according to the information recorded (selecting records that have a particular value in a selected field, for example, searching for all compounds that inhibited a binding assay by at least about 30%); accordingly, another aspect of the invention is a method of using a computer system to catalog and store information about various chemical compounds. The ability to store and retrieve such information in computerized form allows those of ordinary skill in the art to select compounds for additional testing, including additional analysis of binding ability, biological testing, and testing in animal models or clinical trials of pharmaceutical agents in humans. Moreover, in addition to storing and cataloging information, the database can be used to provide a report, either in electronic form or in the form of a printout, that will facilitate further analysis of selected compounds.

One embodiment of the invention comprises a computing environment; an input device, connected to the computing environment, to receive information from the user; an output device, connected to the computing environment, to provide information to the user; and a plurality of algorithms selectively executed based on at least a portion of the received information, wherein any one of these algorithms analyzes at least a portion of the received information and generates output information, and preferably wherein the output information is communicated via the output device. The computing environment preferably further comprises a communications network; a server connected to the network; and a client connected to the network, wherein the client is part of a client-server architecture and typically is an application that runs on a personal computer or workstation and relies on a server to perform some operations (see Nath, 1995, The Guide To SQL Server, 2nd ed., Addison-Wesley Publishing Co.).

The computing environment of the present invention is advantageously implemented using any multipurpose computer system including those generally referred to as personal computers and mini-computers. Such a computer system will include means for processing input information such as at least one central processor, for example an Intel® processor (including Pentium® Pentium® II, Celeron™, Pentium® II3, Pentium® 4 or the like), or Motorola processor (for example, a PowerPC G3 or PowerPC G4 microprocessor capable of running at speeds up to 533 MHz or higher); a storage device, such as a hard disk, for storing information related to DCTSP and/or substrate polypeptides and/or compounds that alter the binding of DCTSP and substrate (or protease activity of DCTSP); and means for receiving input information. Those of skill in the art recognize that computer technology is changing at a rapid rate; accordingly, new, improved versions of processors are comprehended herein.

The processor, which comprises and/or accesses memory units of the computer system, is programmed to perform analyses of information related to the DCTSP and/or substrate polypeptides and/or compounds that modulate their binding (or protease activity of DCTSP). This programming may be permanent, as in the case where the processor is a dedicated PROM (programmable read-only memory) or EEPROM (electrically erasable programmable read-only memory), or it may be transient in which case the programming instructions are loaded from the storage device or from a floppy diskette or other transportable computer-readable media. The computing environment further preferably comprises a user interface such as a Unix/X-Window interface, a Microsoft Windows interface, or a Macintosh operating system interface.

Preferably, the computing environment further includes an optical disk for storing data, a printer for providing a hard copy of the data, and a monitor or video display unit to facilitate user input of information and to display both input and output information. The output information may be output from the processor within the computer system in print form using a printer; on a video display unit; or via a communications link or network to another processor or client application.

Antibodies

Antibodies that are immunoreactive with the polypeptides of the invention are provided herein. Such antibodies specifically bind to the polypeptides via the antigen-binding sites of the antibody (as opposed to non-specific binding). Thus, the polypeptides, fragments, variants, fusion proteins, etc., as set forth above may be employed as "immunogens" in producing antibodies immunoreactive therewith. More specifically, the polypeptides, fragment, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, Immuno Biology 3:9 (Garland Publishing Inc., 2nd ed. 1996)). Because folded proteins have complex surfaces, the number of epitopes available is quite numerous; however, due to the conformation of the protein and steric hindrances, the number of antibodies that actually bind to the epitopes is less than the number of available epitopes (C. A. Janeway, Jr. and P. Travers, Immuno Biology 2:14 (Garland Publishing Inc., 2nd ed. 1996)). Epitopes may be identified by any of the methods known in the art.

Thus, one aspect of the present invention relates to the antigenic epitopes of the polypeptides of the invention. Such epitopes are useful for raising antibodies, in particular monoclonal antibodies, as described in more detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides of the invention, whether the epitopes have been isolated or remain part of the polypeptides, both polyclonal and monoclonal antibodies may be prepared by conventional techniques. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Hybridoma cell lines that produce monoclonal antibodies specific for the polypeptides of the invention are also contemplated herein. Such hybridomas may be produced and identified by conventional techniques. One method for producing such a hybridoma cell line comprises immunizing an animal with a polypeptide or a DNA encoding a polypeptide; harvesting spleen cells from the immunized animal; fusing said spleen cells to a myeloma cell line, thereby generating hybridoma cells; and identifying a hybridoma cell line that produces a monoclonal antibody that binds the polypeptide. The monoclonal antibodies may be recovered by conventional techniques.

The monoclonal antibodies of the present invention include chimeric antibodies, e.g., humanized versions of murine monoclonal antibodies. Such humanized antibodies may be prepared by known techniques and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332:323, 1988), Liu et al. (*Proc. Natl. Acad. Sci. USA* 84:3439, 1987), Larrick et al. (*Bio/Technology* 7:934, 1989), and Winter and Harris (*TIPS* 14:139, May, 1993).

In addition to antibodies that can be produced via recombinant methods, human antibodies can be produced in animals that have been genetically manipulated to have human immunoglobulin genes (transgenic animals). Procedures to generate such human antibodies transgenically can be found in GB 2,272,440, U.S. Pat. Nos. 5,569,825 and 5,545,806 and related patents claiming priority therefrom, all of which are incorporated by reference herein.

Antigen-binding fragments of the antibodies, which may be produced by conventional techniques, are also encompassed by the present invention. Examples of such fragments include, but are not limited to, Fab and F(ab')2 fragments. Antibody fragments and derivatives produced by genetic engineering techniques are also provided.

In one embodiment, the antibodies are specific for the polypeptides of the present invention and do not cross-react with other proteins. Screening procedures by which such antibodies may be identified are well known, and may involve immunoaffinity chromatography, for example.

The antibodies of the invention can be used in assays to detect the presence of the polypeptides or fragments of the invention, either in vitro or in vivo. The antibodies also may be employed in purifying polypeptides or fragments of the invention by immunoaffinity chromatography.

EXAMPLES

The following examples are intended to illustrate particular embodiments and not to limit the scope of the invention.

Example 1

Identification of DCTSP, a New Member of the TTSP Family

A putative serine protease was identified in a cDNA library prepared from human dendritic cells (described in U.S. Pat. No. 6,017,729, issued Jan. 25, 2000) and cloned from commercially available libraries (fetal lung and placenta libraries; Clontech, Palo Alto, Calif.). The nucleotide and predicted amino acid sequences of representative full length clones from each library are shown in SEQ ID NOs÷1 and 2. SEQ ID NOs. 3 and 4 are nucleotide and predicted amino acid sequences, respectively, for a splice variant that was also isolated.

The amino acid sequence of the extracellular domain of DCSTP (SEQ ID NO:2) was compared with the corresponding amino acid sequences of other TTSP family members using the GCG "pretty" multiple sequence alignment program, with amino acid similarity scoring matrix= blosum62, gap creation penalty=8, and gap extension penalty=2. The other TTSP family members included AF24350 (Q9JIQ8, Vaarala et al., *J. Pathol.* 193:134, 2001); XP_009774.3; AB038497 (BAB08217, Yamada et al., *Gene* 252:209, 2000); NP_076927.1 (Bonne-Tamir et al., *Am. J. Hum. Genet.* 58:1254; 1996); AF216312 (NP_057509.1 Walrapp et al., *Cancer Res.* 60:2602, 2000); NP_002763.1 (Kitamoto et al., *Proc. Natl. Acad. Sci. USA* 91:7588, 1994); NP_002142.1 (Leytus et al., *Biochemistry* 27:1067, 1988); and NP_058565 (Tomita et al., *J. Biochem.* 124:784, 1998). An alignment of the extracellular domain of DCTSP compared to a consensus sequence is shown in Table 2; the first amino acid of DCTSP shown in Table 2 corresponds to Ser113 of SEQ ID NO:2. Conserved residues (defined as those residues present in at least seven of the nine peptides examined) are shown in bold face; the activation site, catalytic triad and Cys residues believed to be involved in disulphide bonds are underlined.

The amino acid sequence of DCTSP was also analyzed using the MOTIFS program (the Genetics Computer Group, Madison, Wis.), a program that identifies protein motifs by searching protein sequences for regular-expression patterns described in the PROSRME dictionary (compiled and maintained by Dr. Amos Bairoch of the University of Geneva). This analysis indicated the presence of two motifs characteristic of Trypsin family serine proteases: the histidine active site signature [LIVM]-[ST]-A-[STAG]-H-C (the residue at each position is one of the amino acids listed within the bracket, for example, LTAAHC; amino acids 272 through 277 of SEQ ID NO:2) and the serine active site signature [DNSTAGC]-[GSTAPIMVQH]-x(2)-G-[DE]-S-G-[GS]-[SAPHV]-[LIVMFYWH]-[LIVMFYSTANQH]-C (DSCQGDSGGPLVC; amino acids 415 through 427 of SEQ ID NO:2).

Amino acid substitutions and other alterations (deletions, insertions, etc.) to DCTSP amino acid sequences (e.g. SEQ ID NO:2 or 4) are predicted to be more likely to alter or disrupt DCTSP polypeptide activities if they result in changes to the conserved residues of the amino acid sequences as shown in Table 2, and particularly if those changes do not substitute an amino acid of similar structure (such as substitution of any one of the aliphatic residues—Ala, Gly, Leu, Ile, or Val—for another aliphatic residue; likely residues for such substitutions are marked with an asterisk in Table 2), or a residue present in other TTSP polypeptides at that conserved position. Conversely, if a change is made to a DCTSP amino acid sequence resulting in substitution of the residue at that position in another TTSP polypeptide sequence (even if different from that present in the consensus sequence), it is less likely that such an alteration will affect the function of the altered DCTSP polypeptide.

Preferred substitutions in DCTSP include substitution of an aliphatic residue (particularly Leu, Ile or Val) for Phe at amino acid 139, Gln for Lys at amino acid 147; an aliphatic residue (particularly Leu, Ile or Val) for Tyr at amino acid 219, Ser for Gly at amino acid 234, Ser for Thr at amino acid 264, an aliphatic residue (particularly Leu, Ile or Val) for Phe at amino acid 278, a Phe for Val at amino acid 285, a His for Asn at amino acid 313, a Lys for Arg at amino acid 329, an aliphatic residue (particularly Leu, Ile or Val) for Ala at amino acid 343, a Trp for Phe at amino acid 363, a Gly for Asp at amino acid 371, an aliphatic residue (particularly Leu, Ile or Val, more particularly Ile) for Met at amino acid 405, a Tyr for Asp at amino acid 409, an aliphatic residue (particularly Leu, Ile or, more particularly Val) for Arg at amino acid 414, and a Phe for Val at amino acid 460.

TABLE 2

Alignment of the Extracellular Domain of DCTSP and Consensus Sequence

```
                *                                       *    *
    DCTSP    113~SCPKH  AVRCDGVVDC  KLKSDELGC.  ..........  VRFDWDKSLL   146
Consensus    -----SCIP- S-WCDGV-DC  P-GEDE--CV  -----GP---  VRLYGD--LL

*
    DCTSP    KIYSGSSHQW  LPICSSNWND  SYSEKTCQQL  GFESAHRTTE  ..VAHRDFAN   194
Consensus    QVYSSS---W  -PVCSDNWNE  SYS--AC-QM  G--SA-Y-SE  -G---R-GAN

*                                **
    DCTSP    SFSILR....  .......YNS  TIQESLHRSE  ...CPSQRYI  SLQCSH..CG   228
Consensus    SF-KLNVSP-  NLL--D-YTS  -IQ--L-RSS  S--CPSG-VV  SLQCS-QDCG

*             
    DCTSP    LR...A.MTG  RIVGGALASD  SKWPWQVSL.  HFGTTHICGG  TLIDAQWVLT   273
Consensus    VRLNA--MTS  RIVGG--AS-  G-WPWQVSLQ  ---GVHLCGG  SLI-P-WVLT

***
    DCTSP    AAHCFFVTRE  KVLEGWKVYA  G..TSNLHQL  PEAA...SIAE  IIINSNY     316
Consensus    AAHCV-GR--  KPL-GW-VFA  GILT-SLH--  P-A--R-VEK   IIIHPNY---

*         *
    DCTSP    ...TDEEDDY  DIALMRLSKP  LTLSAHIHPA  CLPMHGQTFS  LNETCWITGF   363
Consensus    ----S--KDN  DIALMKLSKP  LTF-DYIQPV  CLPNPGQ-L-  PGTTCWI-GW

*          *           *
    DCTSP    GKTRETDDKT  SPFLREVQVN  LIDFKKCNDY  LVYDSYLTPR  MMCAGDLRGG   413
Consensus    GAT-E--GKT  SPVLQEA-VP  LIDNK-CNSY  -VYDN-ITPR  MICAGYLEGG

*    *
    DCTSP    RDSCQGDSGG  PLVCE....Q  NNRWYLAGVT  SWGTGC.GQR  NKPGVYTKVT   458
Consensus    VDSCQGDSGG  PLVCE----Q  NNRWWL-G-T  SWG-GC-AKA  NKPGVYT-VT DCTSP    EVLPWIYSKM  ESEVRFRKS~  ~~~    477
Consensus    -FL-WIYSQM  -AE-RFRKS-  ---
```

Example 2

Antibodies that Bind Polypeptides of the Invention

This example illustrates a method for preparing monoclonal antibodies that bind DCTSP polypeptides. Other conventional techniques may be used, such as those described in U.S. Pat. No. 4,411,993. Suitable immunogens that may be employed in generating such antibodies include, but are not limited to, purified DCTSP polypeptides, an immunogenic fragment thereof, synthetic peptides derived from DCTAP amino acid sequence, and cells expressing high levels of DCTSP polypeptides or an immunogenic fragment thereof. DNA encoding A DCTSP polypeptide can also be used as an immunogen, for example, as reviewed by Pardoll and Beckerleg in *Immunity* 3: 165, 1995.

Rodents (BALB/c mice or Lewis rats, for example) are immunized with DCTSP polypeptides immunogen emulsified in an adjuvant (such as complete or incomplete Freund's adjuvant, alum, or another adjuvant, such as Ribi adjuvant R700 (Ribi, Hamilton, Mont.)), and injected in amounts ranging from 10–100 micrograms subcutaneously or intraperitoneally. DNA may be given intradermally (Raz et al., 1994, *Proc. Natl. Acad. Sci. USA* 91: 9519) or intamuscularly (Wang et al., 1993, *Proc. Natl. Acad. Sci. USA* 90: 4156); saline has been found to be a suitable diluent for DNA-based antigens. Ten days to three weeks days later, the immunized animals are boosted with additional immunogen and periodically boosted thereafter on a weekly, biweekly or every third week immunization schedule.

Serum samples are periodically taken by retro-orbital bleeding or tail-tip excision to test for DCTSP polypeptides antibodies by dot-blot assay, ELISA (enzyme-linked immunosorbent assay), immunoprecipitation, or other suitable assays, such as FACS analysis of inhibition of binding of DCTSP polypeptides to a DCTSP polypeptide binding partner. Following detection of an appropriate antibody titer, positive animals are provided one last intravenous injection of DCTSP polypeptides in saline. Three to four days later, the animals are sacrificed, and spleen cells are harvested and fused to a murine myeloma cell line, e.g., NS1 or preferably P3X63Ag8.653 (ATCC CRL-1580). These cell fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells may be screened by ELISA for reactivity against purified DCTSP polypeptides by adaptations of the techniques disclosed in Engvall et al., (*Immunochem.* 8: 871, 1971) and in U.S. Pat. No. 4,703,004. A preferred screening technique is the antibody capture technique described in Beckmann et al., (*J. Immunol.* 144: 4212, 1990). Positive hybridoma cells can be injected intraperitoneally into syngeneic rodents to produce ascites containing high concentrations (for example, greater than 1 milligram per milliliter) of anti-DCTSP polypeptides monoclonal antibodies. Alternatively, hybridoma cells can be grown in vitro in flasks or roller bottles by various techniques. Monoclonal antibodies can be purified by ammonium sulfate precipitation, followed by gel exclusion chromatography. Alternatively, affinity chromatography based upon binding of antibody to protein A or protein G can also be used, as can affinity chromatography based upon binding to DCTSP polypeptides.

Example 3

Antisense Inhibition of DCTSP Nucleic Acid Expression

In accordance with the present invention, a series of oligonucleotides are designed to target different regions of the DCTSP mRNA molecule, using the nucleotide sequence of SEQ ID NOs: 1 or 3 as the basis for the design of the oligonucleotides. The oligonucleotides are selected to be approximately 10, 12, 15, 18, or more preferably 20 nucleotide residues in length, and to have a predicted hybridization temperature that is at least 37 degrees C. Preferably, the oligonucleotides are selected so that some will hybridize toward the 5' region of the mRNA molecule, others will hybridize to the coding region, and still others will hybridize to the 3' region of the mRNA molecule.

The oligonucleotides may be oligodeoxynucleotides, with phosphorothioate backbones (internucleoside linkages) throughout, or may have a variety of different types of internucleoside linkages. Generally, methods for the preparation, purification, and use of a variety of chemically modified oligonucleotides are described in U.S. Pat. No. 5,948,680. As specific examples, the following types of nucleoside phosphoramidites may be used in oligonucleotide synthesis: deoxy and 2'-alkoxy amidites; 2'-fluoro amidites such as 2'-fluorodeoxyadenosine amidites, 2'-fluorodeoxyguanosine, 2'-fluorouridine, and 2'-fluorodeoxycytidine; 2'-O-(2-methoxyethyl)-modified amidites such as 2,2'-anhydro[1-(beta-D-arabino-furanosyl)-5-methyluridine], 2'-O-methoxyethyl-5-methyluridine, 2'-O-methoxyethyl-5'-O-dimethoxytrityl-5-methyluridine, 3'-O-acetyl-2'-O-methoxy-ethyl-5'-O-dimethoxytrityl-5-methyluridine, 3'-O-acetyl-2'-O-methoxyethyl-5'-O-dimethoxytrityl-5-methyl-4-triazoleuridine, 2'-O-methoxyethyl-5'-O-dimethoxy-trityl-5-methylcytidine, N4-benzoyl-2'-O-methoxyethyl-5'-O-dimethoxytrityl-5-methyl-cytidine, and N4-benzoyl-2'-O-methoxyethyl-5'-O-di-methoxytrityl-5-methylcytidine-3'-amidite; 2'-O-(aminooxyethyl) nucleoside amidites and 2'-O-(dimethylaminooxyethyl) nucleoside amidites such as 2'-(dimethylaminooxyethoxy)nucleoside amidites, 5'-O-tert-butyldiphenylsilyl-$O^2$-2'-anhydro-5-methyluridine, 5'-O-tert-butyl-diphenylsilyl-2'-O-(2-hydroxyethyl)-5-methyluridine, 2'-O-([2-phthalimidoxy)ethyl]-5'-t-butyldiphenyl-silyl-5-methyluridine, 5'-O-tert-butyldiphenylsilyl-2'-O-[(2-formadoximinooxy)ethyl]-5-methyluridine, 5'-O-tert-butyldiphenylsilyl-2'-O-[N,N-dimethylaninooxyethyl]-5-methyluridine, 2'-O-(dimethylaminooxy-ethyl)-5-methyluridine, 5'-O-DMT-2'-O-(dimethylaminooxyethyl)-5-methyluridine, and 5'-O-DMF-2'-O-(2-N,N-dimethylaminooxyethyl)-5-methyluridine-3'-[(2-cyanoethyl)-N,N-diisopropyl-phosphor-amidite]; and 2'-(aminooxyethoxy) nucleoside amidites such as N2-isobutyryl-6-O-diphenyl-carbamoyl-2'-O-(2-ethylacetyl)-5'-O-(4,4'-dimethoxytrityl)guanosine-3'-[(2-cyanoethyl)-N,N-diisopropylphosphormidite].

Modified oligonucleosides may also be used in oligonucleotide synthesis, for example methylenemethylimino-linked oligonucleosides, also called MMI-linked oligonucleosides; methylene-dimethylhydrazo-linked oligonucleosides, also called MDH-linked oligonucleosides; methylene-carbonylamino-linked oligonucleosides, also called amide-3-linked oligonucleosides; and methylene-aminocarbonyl-linked oligonucleosides, also called amide-4-linked oligonucleosides, as well as mixed backbone compounds having, for instance, alternating MMI and P=O or P=S linkages, which are prepared as described in U.S. Pat. Nos. 5,378,825, 5,386,023, 5,489,677, 5,602,240 and 5,610,289. Formacetal- and thioformacetal-linked oligonucleosides may also be used and are prepared as described in U.S. Pat. Nos. 5,264,562 and 5,264,564; and ethylene oxide linked oligonucleosides may also be used and are prepared as described in U.S. Pat. No. 5,223,618. Peptide nucleic acids (PNAs) may be used as in the same manner as the oligonucleotides described above, and are prepared in accordance with any of the various procedures referred to in Peptide Nucleic Acids (PNA): Synthesis, Properties and Potential Applications, Bioorganic & Medicinal Chemistry, 1996, 4, 5–23; and U.S. Pat. Nos. 5,539,082, 5,700,922, and 5,719,262.

Chimeric oligonucleotides, oligonucleosides, or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers". Some examples of different types of chimeric oligonucleotides are: [2'-O-Me]--[2'-deoxy]--[2'-O-Me] chimeric phosphorothioate oligonucleotides, [2'-O-(2-methoxyethyl)]--[2'-deoxy]--[2'-O-(methoxyethyl)] chimeric phosphorothioate oligonucleotides, and [2'-O-(2-methoxy-ethyl) phosphodiester]--[2'-deoxy phosphoro-thioate]--[2'-O-(2-methoxyethyl)phosphodiester] chimeric oligonucleoides, all of which may be prepared according to U.S. Pat. No. 5,948,680. In one preferred embodiment, chimeric oligonucleotides ("gapmers") 18 nucleotides in length are utilized, composed of a central "gap" region consisting of ten 2'-deoxynucleotides, which is flanked on both sides (5' and 3' directions) by four-nucleotide "wings". The wings are composed of 2'-methoxyethyl (2'-MOE) nucleotides. The internucleoside (backbone) linkages are phosphorothioate (P=S) throughout the oligonucleotide. Cytidine residues in the 2'-MOE wings are 5-methylcytidines. Other chimeric oligonucleotides, chimeric oligonucleosides, and mixed chimeric oligonucleo-tides/oligonucleosides are synthesized according to U.S. Pat. No. 5,623,065.

Oligonucleotides are preferably synthesized via solid phase P(III) phosphoramidite chemistry on an automated synthesizer capable of assembling 96 sequences simultaneously in a standard 96 well format. The concentration of oligonucleotide in each well is assessed by dilution of samples and UV absorption spectroscopy. The full-length integrity of the individual products is evaluated by capillary electrophoresis, and base and backbone composition is confirmed by mass analysis of the compounds utilizing electrospray-mass spectroscopy.

The effect of antisense compounds on target nucleic acid expression can be tested in any of a variety of cell types provided that the target nucleic acid is present at measurable levels. This can be routinely determined using, for example, PCR or Northern blot analysis. Cells are routinely maintained for up to 10 passages as recommended by the supplier. When cells reached 80% to 90% confluency, they are treated with oligonucleotide. For cells grown in 96-well plates, wells are washed once with 200 microliters OPTI-MEM-1 reduced-serum medium (Gibco BRL) and then treated with 130 microliters of OPTI-MEM-1 containing 3.75 g/mL LIPOFECTIN (Gibco BRL) and the desired oligonucleotide at a final concentration of 150 nM. After 4 hours of treatment, the medium is replaced with fresh medium. Cells are harvested 16 hours after oligonucleotide treatment. Preferably, the effect of several different oligonucleotides should be tested simultaneously, where the oligonucleotides hybridize to different portions of the target nucleic acid molecules, in order to identify the oligonucleotides producing the greatest degree of inhibition of expression of the target nucleic acid.

Antisense modulation of DCTSP nucleic acid expression can be assayed in a variety of ways known in the art. For example, DCTSP mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA.

Methods of RNA isolation and Northern blot analysis are taught in, for example, Ausubel, F. M. et al., Current Protocols in Molecular Biology, Volume 1, pp. 4.1.1–4.2.9 and 4.5.1–4.5.3, John Wiley & Sons, Inc., 1996. Real-time quantitative (PCR) can be conveniently accomplished using the commercially available ABI PRISM 7700 Sequence Detection System, available from PE-Applied Biosystems, Foster City, Calif. and used according to manufacturer's instructions. This fluorescence detection system allows high-throughput quantitation of PCR products. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE or FAM, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular (six-second) intervals by laser optics built into the ABI PRISM 7700 Sequence Detection System. In each assay, a series of parallel reactions containing serial dilutions of mRNA from untreated control samples generates a standard curve that is used to quantitate the percent inhibition after antisense oligonucleotide treatment of test samples. Other methods of quantitative PCR analysis are also known in the art.

DCTSP protein levels can be quantitated in a variety of ways well known in the art and described herein, such as immunoprecipitation, Western blot analysis (immunoblotting), ELISA, or fluorescence-activated cell sorting (FACS). Antibodies directed to DCTSP polypeptides can be prepared via conventional antibody generation methods such as those described herein. Immunoprecipitation methods, Western blot (immunoblot) analysis, and enzyme-linked immunosorbent assays (ELISA) are standard in the art (see, for example, Ausubel, F. M. et al., Current Protocols in Molecular Biology, Volume 2, pp. 10.16.1–10.16.11, 10.8.1–10.8.21, and 11.2.1–11.2.22, John Wiley & Sons, Inc., 1991).

Example 4

Antibodies that Bind Polypeptides of the Invention

This example illustrates a method for preparing monospecific, polyclonal antibodies that bind DCTSP polypeptides. Suitable immunogens that may be employed in generating such antibodies include, but are not limited to, purified DCTSP polypeptides, an immunogenic fragment thereof, synthetic peptides derived from DCTSP amino acid sequence, and cells expressing high levels of DCTSP polypeptides or an immunogenic fragment thereof. DNA encoding a DCTSP polypeptide can also be used as an immunogen, for example, as reviewed by Pardoll and Beckerleg in *Immunity* 3: 165, 1995.

Rabbits or other mammals (for example, guinea pigs) are immunized with DCTSP polypeptides immunogen emulsified in an adjuvant (such as complete or incomplete Freund's adjuvant, alum, or another adjuvant, such as Ribi adjuvant R700 (Ribi, Hamilton, Mont.)), and injected in amounts ranging from 10–100 micrograms subcutaneously or intraperitoneally. DNA may be given intradermally (Raz et al., 1994, *Proc. Natl. Acad. Sci. USA* 91: 9519) or intamuscularly (Wang et al., 1993, *Proc. Natl. Acad. Sci. USA* 90: 4156); saline has been found to be a suitable diluent for DNA-based antigens. Ten to about twenty-one days later, the immunized animals are boosted with additional immunogen and periodically boosted thereafter on a weekly, biweekly or every third week immunization schedule.

Serum samples are periodically taken to test for DCTSP polypeptides antibodies by suitable assay(s). Following detection of an appropriate antibody titer, a protein A or protein G column is used to purify immunoglobulins from serum or plasma from the animal(s). Monospecific antibodies are then purified from the immunoglobulins by affinity purification using a single peptide or protein.

In this manner, a monospecific antibody against a peptide comprising the C-terminal region of DCTSP was raised. The immunogen comprised amino acids 455 through 477 of SEQ ID NO:2, and also contained, at the N-terminus, the sequence Gly Cys Gly. The Gly Cys Gly was added to enable covalent coupling of the peptide to a hapten (maleimide activated keyhole limpet hemocyanin [KLH]) via a disulfide bond between the Cys in the Gly Cys Gly sequence and the maleimide sulfhydryl. The monospecific antibody preparation was affinity purifed using the same peptide that had been used as the immunogen. The ability of the isolated monospecfic antibody preparation to bind DCTSP was confirmed by Western blot analysis using DCTSP protease domain (amino acid 227 to 477) over-expressed in COS cells. Monoclonal antibodies that bind a peptide comprising amino acids 455 through 477 of SEQ ID NO:2 or an immunogenic fragment thereof are generated in a similar manner, as described herein in Example 2.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. An isolated DCTSP (Dendritic Cell Transmembrane Serine Protease) polypeptide selected from the group consisting of:
   (a) a polypeptide comprising amino acids 1 through 477 of SEQ ID NO:2; and
   (b) a fragment of the polypeptide of (a), comprising amino acids x through y of SEQ ID NO:2, wherein x represents an integer from 1 to 47, inclusive, and y represents an integer from 470 to 477, inclusive, the fragment having DCTSP activity.

2. The DCTSP polypeptide of claim 1, which further comprises a peptide selected from the group consisting of an immunoglobulin Fc domain, an immunoglobulin Fc mutein, a FLAG® tag, a peptide comprising at least about 6 His residues, a leucine zipper, and combinations thereof.

3. An isolated fragment of a DCTSP polypeptide selected from the group consisting of:
   (a) a polypeptide consisting of amino acids 1 to x of SEQ ID NO:2, wherein x represents an integer from 75 to 95, inclusive of SEQ ID NO:2; and
   (b) a polypeptide comprising the polypeptide of (a) and a peptide selected from the group consisting of an immunoglobulin Fc domain, an immunoglobulin Fc mutein, a FLAG® tag, a peptide comprising at least about 6 His residues, a leucine zipper, and combinations thereof.

4. The fragment of claim 3 wherein x is 75.

* * * * *

UNITED STATES PATENT AND TRADEMARK OFFICE
CERTIFICATE OF CORRECTION

| | |
|---|---|
| PATENT NO. | : 6,794,173 B2 |
| APPLICATION NO. | : 10/177661 |
| DATED | : September 21, 2004 |
| INVENTOR(S) | : Dirk M. Anderson and G. Duke Virca |

It is certified that error appears in the above-identified patent and that said Letters Patent is hereby corrected as shown below:

Column 10, line 4 "Be" should read -- Ile --.

Column 22, line 38, "Cont." should read -- CT --.

Column 27, line 22, "PROSRME" should read -- PROSITE --.

Column 30, line 45, "5'-O-DMF" should read -- 5'-O-DMT --.

Signed and Sealed this

Twelfth Day of September, 2006

JON W. DUDAS
*Director of the United States Patent and Trademark Office*